US008961813B2

(12) United States Patent
Kiely et al.

(10) Patent No.: US 8,961,813 B2
(45) Date of Patent: Feb. 24, 2015

(54) HYDROXYCARBOXYLIC ACIDS AND SALTS

(75) Inventors: Donald E. Kiely, Missoula, MT (US); Kirk R. Hash, Drummond, MT (US); Kylie Kramer-Presta, Missoula, MT (US); Tyler N. Smith, Missoula, MT (US)

(73) Assignee: The University of Montana, Missoula, MT (US)

( * ) Notice: Subject to any disclaimer, the term of this patent is extended or adjusted under 35 U.S.C. 154(b) by 0 days.

(21) Appl. No.: 13/586,953

(22) Filed: Aug. 16, 2012

(65) Prior Publication Data
US 2012/0305832 A1 Dec. 6, 2012

Related U.S. Application Data

(60) Division of application No. 13/277,896, filed on Oct. 20, 2011, which is a division of application No. 12/422,135, filed on Apr. 10, 2009, which is a continuation-in-part of application No. 11/890,760, filed on Aug. 6, 2007, now Pat. No. 7,692,041.

(60) Provisional application No. 60/836,329, filed on Aug. 7, 2006.

(51) Int. Cl.
C09K 3/18 (2006.01)
C23F 11/12 (2006.01)
C04B 24/06 (2006.01)
C04B 103/61 (2006.01)

(52) U.S. Cl.
CPC .............. *C23F 11/126* (2013.01); *C09K 3/185* (2013.01); *C04B 24/06* (2013.01); *C04B 2103/61* (2013.01)
USPC .......................................................... 252/70

(58) Field of Classification Search
CPC ..................................................... C09K 3/185
USPC ........... 127/34; 106/14.13, 14.14, 14.24, 823; 252/70
See application file for complete search history.

(56) References Cited

U.S. PATENT DOCUMENTS

| | | |
|---|---|---|
| 1,520,885 A | 12/1924 | Rankin |
| 2,314,831 A | 3/1943 | Kamlet |
| 2,380,196 A | 7/1945 | Solomon |
| 2,419,019 A | 4/1947 | Hales |
| 2,436,659 A | 2/1948 | Mehltretter et al. |
| 2,472,168 A | 6/1949 | Mehltretter |
| 2,529,177 A | 11/1950 | Nieland |
| 2,529,178 A | 11/1950 | Nieland |
| 3,242,207 A | 3/1966 | Ulrich et al. |
| 3,346,623 A | 10/1967 | Young |
| 3,362,885 A * | 1/1968 | Harned .......................... 435/111 |
| 3,589,859 A | 6/1971 | Foroulis |
| 3,652,396 A | 3/1972 | Tanaka et al. |
| 3,711,246 A | 1/1973 | Foroulis |
| 3,798,168 A | 3/1974 | Tumerman et al. |
| 3,819,659 A | 6/1974 | Baldwin et al. |
| 3,951,877 A | 4/1976 | Okumura et al. |
| 4,000,083 A | 12/1976 | Heesen |
| 4,108,790 A | 8/1978 | Foroulis |
| 4,120,655 A | 10/1978 | Crambes |
| 4,129,423 A | 12/1978 | Rubin |
| 4,485,100 A | 11/1984 | Hochstrasser et al. |
| 4,512,552 A | 4/1985 | Katayama et al. |
| 4,833,230 A | 5/1989 | Kiely et al. |
| 4,834,793 A | 5/1989 | Schneider et al. |
| 4,845,123 A | 7/1989 | Walaszek et al. |
| 5,017,485 A | 5/1991 | Bringer-Meyer et al. |
| 5,256,294 A | 10/1993 | van Reis |
| 5,264,123 A | 11/1993 | Bailey |
| 5,312,967 A | 5/1994 | Kiely et al. |
| 5,329,044 A | 7/1994 | Kiely et al. |
| 5,330,683 A | 7/1994 | Sufrin |
| 5,364,644 A | 11/1994 | Walaszek |
| 5,376,499 A | 12/1994 | Hammerschmidt et al. |
| 5,434,233 A | 7/1995 | Kiely et al. |
| 5,473,035 A | 12/1995 | Kiely et al. |
| 5,478,374 A | 12/1995 | Kiely |
| 5,531,931 A | 7/1996 | Koefod |
| 5,561,160 A | 10/1996 | Walaszek |
| 5,562,828 A | 10/1996 | Olsen et al. |
| 5,599,977 A | 2/1997 | Kiely et al. |
| 5,891,225 A | 4/1999 | Mishra |
| 5,958,867 A | 9/1999 | Lamberti et al. |
| 5,999,977 A | 12/1999 | Riddle |
| 6,049,004 A | 4/2000 | Kiely et al. |
| 6,156,226 A | 12/2000 | Klyosov et al. |
| 6,372,410 B1 | 4/2002 | Ikemoto et al. |
| 6,498,269 B1 | 12/2002 | Merbouh et al. |

(Continued)

FOREIGN PATENT DOCUMENTS

| | | |
|---|---|---|
| CA | 2188063 | 4/1998 |
| CN | 1131651 | 9/1996 |

(Continued)

OTHER PUBLICATIONS

Yahiro et al, "Efficient Acid Production from Raw Corn Starch", Journal of Fermentation and Bioengineering, vol. 84(4), pp. 375-377, (1997).*

(Continued)

*Primary Examiner* — David M Brunsman
(74) *Attorney, Agent, or Firm* — Michael Best & Friedrich LLP

(57) ABSTRACT

Compositions which inhibit corrosion and alter the physical properties of concrete (admixtures) are prepared from salt mixtures of hydroxycarboxylic acids, carboxylic acids, and nitric acid. The salt mixtures are prepared by neutralizing acid product mixtures from the oxidation of polyols using nitric acid and oxygen as the oxidizing agents. Nitric acid is removed from the hydroxycarboxylic acids by evaporation and diffusion dialysis.

25 Claims, No Drawings

(56) References Cited

U.S. PATENT DOCUMENTS

| | | | |
|---|---|---|---|
| 6,686,325 | B2 | 2/2004 | Hoyt et al. |
| 6,827,776 | B1 | 12/2004 | Boggs |
| 6,831,195 | B2 | 12/2004 | Nishimura et al. |
| 6,843,931 | B2 | 1/2005 | Sapienza |
| 6,861,009 | B1 | 3/2005 | Leist |
| 6,894,135 | B2 | 5/2005 | Kiely et al. |
| 6,919,478 | B2 | 7/2005 | Kawato et al. |
| 7,125,441 | B1 | 10/2006 | Furman et al. |
| 7,314,906 | B2 | 1/2008 | Kiely et al. |
| 7,658,861 | B2 | 2/2010 | Koefod |
| 7,692,041 | B2 | 4/2010 | Kiely et al. |
| 8,153,573 | B2 | 4/2012 | Miralles et al. |
| 8,679,364 | B2 * | 3/2014 | Pylkkanen ..................... 252/70 |
| 2003/0109394 | A1 | 6/2003 | Ruhr et al. |
| 2003/0168625 | A1 | 9/2003 | Sapienza et al. |
| 2003/0176305 | A1 | 9/2003 | Hoyt et al. |
| 2004/0025908 | A1 | 2/2004 | Douglas et al. |
| 2004/0028655 | A1 | 2/2004 | Nelson et al. |
| 2004/0185562 | A1 | 9/2004 | Schroeder et al. |
| 2004/0188092 | A1 | 9/2004 | Santra |
| 2005/0202981 | A1 | 9/2005 | Eveland et al. |
| 2005/0202989 | A1 | 9/2005 | Wilson |
| 2005/0230658 | A1 | 10/2005 | Koefod |
| 2005/0071431 | A1 | 11/2005 | Roddy |
| 2007/0037727 | A1 | 2/2007 | Fiore et al. |
| 2007/0278446 | A1 | 12/2007 | Koefod |
| 2008/0033205 | A1 | 2/2008 | Kiely et al. |
| 2008/0099716 | A1 | 5/2008 | Koefod |
| 2008/0287334 | A1 | 11/2008 | Smith et al. |
| 2008/0302737 | A1 | 12/2008 | Denkewicz, Jr. et al. |
| 2009/0131259 | A1 | 5/2009 | Kiely |
| 2009/0250653 | A1 | 10/2009 | Kiely |
| 2010/0041574 | A1 | 2/2010 | Warkotsch et al. |
| 2010/0130774 | A1 | 5/2010 | Wan et al. |
| 2010/0191002 | A1 | 7/2010 | Kiely |
| 2011/0263905 | A1 | 10/2011 | Purola |
| 2011/0269662 | A1 | 11/2011 | Miralles |
| 2012/0035356 | A1 | 2/2012 | Kiely |
| 2012/0119152 | A1 | 5/2012 | Smith |
| 2012/0277141 | A1 | 11/2012 | Smith |
| 2012/0295986 | A1 | 11/2012 | Smith |
| 2014/0275621 | A1 | 9/2014 | Donen |
| 2014/0275622 | A1 | 9/2014 | Donen |
| 2014/0275623 | A1 | 9/2014 | Donen |

FOREIGN PATENT DOCUMENTS

| | | |
|---|---|---|
| CN | 1970488 | 5/2007 |
| DE | 2016686 | 11/1970 |
| DE | 1929968 | 12/1970 |
| DE | 117492 | 1/1976 |
| DE | 3331751 | 3/1984 |
| DE | 3519884 | 1/1986 |
| EP | 0652305 | 5/1995 |
| EP | 0758678 | 2/1997 |
| EP | 0819653 | 1/1998 |
| EP | 1201617 | 5/2002 |
| FR | 2054945 | 6/1971 |
| FR | 2115300 | 8/1972 |
| GB | 866840 | 5/1961 |
| GB | 2405636 | 9/2003 |
| JP | 47048091 | 12/1972 |
| JP | S51011030 | 1/1976 |
| JP | 51041578 | 11/1976 |
| JP | 54043840 | 4/1979 |
| JP | S57192270 | 11/1982 |
| JP | S58091174 | 5/1983 |
| JP | 60-50188 | 3/1985 |
| JP | S60050188 | 3/1985 |
| JP | 60108352 | 6/1985 |
| JP | 60112676 | 6/1985 |
| JP | 63248782 | 10/1988 |
| JP | 04214057 | 8/1992 |
| JP | H06306652 | 11/1994 |
| JP | H09104687 | 4/1997 |
| JP | 2004123465 | 4/2003 |
| JP | 2003306369 | 10/2003 |
| JP | 2008054806 | 3/2008 |
| KR | 20020066275 | 8/2002 |
| PL | 98149 | 8/1978 |
| RO | 69880 | 4/1981 |
| WO | 92/07108 | 4/1992 |
| WO | WO 00/34221 | 6/2000 |
| WO | WO 2004/052958 | 6/2004 |
| WO | WO 2004/052959 | 6/2004 |
| WO | WO 2008/021054 | 2/2008 |
| WO | WO 2009/065143 | 5/2009 |
| WO | WO 2012/065001 | 5/2012 |
| WO | WO 2012/145688 | 10/2012 |
| WO | WO 2012/145690 | 10/2012 |
| WO | 2013/090090 | 6/2013 |

OTHER PUBLICATIONS

United States Patent Office Action for U.S. Appl. No. 13/452,560 dated Dec. 4, 2013 (11 pages).

Abbadi et al., New Ca-Sequestering Materials Based on the Oxidation of the Hydrolysis Products of Lactose, Green Chem, 1999, 231-235.

Abd El Kader, J.M. et al., ""Corrosion inhibition of mild steel by sodium tungstate in neutral solution. Part 3. Coinhibitors and synergism,"" British Corrosion Journal, 33, 152-157 (1998) Chem Abstr AN 1998:796697.

Abdallah, M. "Sodium gluconate, triethanolamine and their mixtures as corrosion inhibitors of carbon steel in 3.5% NaCl solution," Journal of the Electrochemical Society of India, 48, 121-127, (1999) Chem Abst AN 1999:374923.

Allcock, H.R. et al., "Effect of nonstoichiometric reactant ratios on linear condensation polymers," Contemporary Polymer Chemistry, 2nd Edition, Prentice-Hall, New Jersey (1990) Part II, 274-275.

Billmeyer, F.W., Jr., "Molecular weight and molecular-weight distribution," Textbook of Polymer Science 3rd Edition, Wiley Interscience, New York (1984) 38-47.

Cantrell, C. E., et al., ""s-Dicarbonyl Sugars. 5. A Novel Synthesis of a Branched-Chain Cyclitol,"" J. Org. Chem. (1977) 42(22):3562-3567.

Carter, Andy, "Modifications in the Preparation of Glucaric Acid and Some 4-alkyl-4-azaheptane-1,7-diamines," 1998, Thesis, University of Alabama, Birmingham, AL, p. 18-20.

Chen, L., "Experimental and Theoretical Studies Concerned with Synthetic Acyclic Carbohydrate Based Polyamides," A Dissertation, University of Alabama at Birmingham (1992).

Chen, L. et al., "Synthesis of steroregular head-tail hydroxylated nylons derived from D-glucose," J. Org. Chem. (1996) 61:5847-5851.

Collepardi, M.M.; "Concrete Admixture Handbook: Properties, Science and Technology", 2nd Edition, Ramachandran,V.S. Editor,Noyes Publications, Park Ridge,NJ (1995) p. 286-409.

Cotton, F.A. et al., Advanced Inorganic Chemistry, 1988, p. 341-353, John Wiley and Sons, New York.

CRC Handbook of Chemistry and Physics, edited by Weast et al., 64th Edition, 1983-84, Boca Raton, Florida, p. B-117.

Hashimoto et al., "Macromolecular synthesis from caccharic lactones. Ring-opening polyaddition of D-glucaro- and D-mannaro-1,4:6,3-dilactones with alkylenediamines," J. Polym. Sci. Part A: Polym. Chem. (1993) 31:3141-3149.

Hashimoto, K. et al., "Ring-opening polyaddition of D-glucaro-1,4:6,3-dilactone with p-zylylenediamine," Macromol. Chem. Rapid Commun. (1990) 11:393-396.

Haworth et al., "Lactones of mannosaccharic acid, Part I. 2: 5-dimethyl Δ4-manno-saccharo-3: 6-lactone 1-methyl ester, an analogue of ascorbic acid," J. Chem. Soc. London (1944) 56:217-224.

Haworth, W.N. et al., ""Some Derivatives of Glucosaccharic Acids,"" J. Chem. Soc. (1944) 25:65-76.

Kiely et al., "Hydroxylated nylons based on unprotected esterified D-glucaric acid by simple condensation reactions," J. Am. Chem. Soc. (1994) 116(2):571-578.

(56) References Cited

OTHER PUBLICATIONS

Kirk-Othmer Encyclopedia of Chemical Technology, 3rd Edition, Wiley, New York, vol. 16, 617-634, "Hydrocarbon Resins" to "Hypnotics, Sedatives, Anticonvulsants".

Korzh, E.N. et al., "Acidity and corrosion activity of brine refrigeratnts based on calcium chloride," Zhurnal Prikladnoi Khimii Journal (Russian) (1981) 54:2404-2407, Chern. Abstr. AN 1982-147045.

Lachman, A., "Dihydroxy-Tartaric Acid," Amer. Chern. Soc. (1921) 43:2091-2097.

Lewis, B.A. et al., Chapter 13, "Galactaric acid and its derivatives," Methods in Carbohydrate Chemistry, R.L. Whistler et al., editors, (1953) II:38-46.

Lin, "Diverse Applications of Carbohydrate Acids in Organic Synthesis," A Dissertation, University of Alabama at Birmingham (1987) p. 48-50, 72-74.

Lowe et al., Soaps and Detergents—The Inorganic Components, J. Am. Oil Chem. Soc., 1978, 55, 32-35.

Mainhardt, H., "N20 Emissions from Adipic Acid and Nitric Acid Production," IPCC Good Practice Guidance and Uncertainty Management in National Greenhouse Gas Inventories (2001).

Marukame, K., S.Fushoku Burnon linkai Shiryo(Nippon Xairyo Gakkai), journal written in Japanese, 173, 1-8, (1993) Chern. Abstr. AN 1993:543767.

Mehletretter, C.L., "D-Giucaric Acid," Methods in Carbohydrate Chemistry, 1963, p. 46-48, vol. II, Academic Press, New York.

Mehltretter, C.L. et al., "Saccharic and Oxalic Acids by the Nitric Acid Oxidation of Dextrose," Agric. and Food Chern. (1953) 1(12):779-783.

Merbough, N. et al., "4-AcNH-tempo-Catalyzed Oxidation of Aldoses to Aldaric Acids Using Chlorine or Bromine as Terminal Oxidants," J. Carbohydr. Chem., 2002, 21:.66-77.

Mor, E. et al., "Steel corrosion inhibition in seawater by calcium organic compounds," Annali deii'University di Ferrara, Sezione 5; Chimica Pura ed Applicata, Journal in French (1971),Chem Abstr AN 1971:414090.

Mor, E. et al., "Zinc gluconate as an inhibitor of the corrosion of mild steel in sea water," Lab Corros. Mar. Met, British Corrosion Journal (1976) 11:199-203 Chern. Abstr. AN 1977:129710.

Mustakas, G.C. et al., "Potassium Acid Saccharate by Nitric Acid Oxidation of Dextrose," Industrial and Engineering Chemistry, Mar. 1954, 427-434.

National Association of Corrosion Engineers (NACE) Standard TM0169-95 as Modified by the Pacific Northwest States, Test Method B, Revision (Apr. 2006).

Ogata, N. et al., "Active polycondensation of diethyl 2,3,4,5-tetrahydroxyadipate with diamines," J. Polym. Sci. Polym. Chem. Ed. (1976) 14:783-792.

Ogata, N. et al., "Copolycondensation of hydroxyl diesters and active diesters with hexamethylenediamine," J. Polym. Sci. Polym. Chem. Ed. (1977) 15:1523-1526.

Ogata, N. et al., "Polycondensation reaction of dimethyl tartrate with hexamethylenediamine in the presence of various matrices," J. Polym. Sci. Polym. Chem. Ed. (1980) 18:939-948.

Ogata, N. et al., "Synthesis of hydrophilic polyamide by active polycondensation," J. Polym. Sci. Polym. Lett. Ed. (1974) 12:355-358.

Ogata, N. et al., "Synthesis of hydrophilic polymide from L-tartarate and diamines by active polycondensation," J. Polym. Sci. Polym. Chem. Ed. (1975) 13:1793-1801.

Ogata, N. et al., "Synthesis of polyamides through active diesters," J. Polym. Sci., Polym. Chem. Ed. (1973) 11:1095-1105.

Ogata, N. et al., "Synthesis of polyesters from active diesters," J. Polym. Sci. Chem. Ed. (1973) 11:2537-2545.

Ogata, N., "New polycondensation systems," Polym. Prepr. (1976) 17:151-156.

Pamuk et al. "The preparation of D-glucaric acid by oxidation of molasses in packed beds" Journal of Chemical Technology and Biotechnology (2001) 76:186-190.

Roper, H., "Selection oxidation of D-glucose: chiral intermediates for industrial utilization," Starch/Starke (1990) 42(9):342-349.

Stanek, J. et al., "Monosaccharide dicarboxylic acids," The Monosaccharides, Academic Press, New York and London (1963) Chapter XXXII, p. 741-752.

Styron, S.D. et al., "MM3(96) conformational analysis of D-glucaramide and x-ray crystal structures of three D-glucaric acid derivatives—models for synthetic poly(alkylene D-glucaramides)," J. Carb. Chem. (2002) 21(1&2):27-51.

Sukhotin,A.M. et al., "Corrosion inhibitor for steel in calcium chloride solutions," Zashchita Mettalov, Journal in Russion (1982) 18:268-70, Chem Ab 1982:476671.

Van Duin et al., Studies on borate esters. Part 8. Interactions of cations with oxyacid anion-bridged esters of D-glucarate in alkaline media, J. Chem. Soc. Dalton Trans., 1987, 8, 2051-2057.

Van Duin et al., Synergic Coordination of Calcium in Borate-Polyhydroxycarboxylate Systems, Carb. Res., 1987, 162, 65-78.

Van Duin, M. et al., "Studies on borate esters. Part 5. The system glucarate borate calcium (II) as studied by 1H, 11B, and 13C nuclear magnetic resonance spectroscopy," J. Chem. Soc. (1987) 2(4):473-478.

Werpy, T. et al., Top Value Added Chemicals from Biomass, Voil-Results of Screening for Potential, www.osti.gov/bridge, U.S. Dept. of Energy, Oak Ridge, TN (2004) 76 pages.

Wilham et al., Organic Acids as Builders in Linear Alkylbenzene Sulfonate Detergent Formulations, J. Am. Oil Chem. Soc., 1971, 48(11), 682-683.

Wisconsin Biorefiners Development Initiative and references therein, Biorefining Processes-Fermentation of 6-Carbon Sugars and Starchs, www.wisbiorefine.org/proc/ferments.pdr (Feb. 5, 2007).

Wrubl, C. et al., "Zinc gluconate as an inhibitor of the corrosion of copper and zinc in seawater," 1st Corros. Mar Met, British Corrosion Journal (1983) 18:142-147, Chem. Abstr. AN 1984:11228.

International Preliminary Report on Patentability for Application No. PCT/US2007/017493 dated Feb. 10, 2009.

International Preliminary Report on Patentability for Application No. PCT/US2008/083831 dated May 18, 2010 (8 pages).

International Preliminary Report on Patentability for Application No. PCT/US2011/060264 dated May 23, 2013 (8 pages).

International Search Report and Written Opinion for Application No. PCT/US2012/034538 dated Jul. 10, 2012 (11 pages).

International Search Report and Written Opinion for Application No. PCT/US2012/034542 dated Jul. 10, 2012 (10 pages).

International Search Report for Application No. PCT/US2003/039733 dated May 13, 2004 (2 pages).

International Search Report for Application No. PCT/US2007/017493 dated Feb. 12, 2008.

International Search Report for Application No. PCT/US2011/060264 dated Feb. 10, 2012.

United States Patent Office Action for U.S. Appl. No. 11/890,760 dated Apr. 16, 2009 (7 pages).

United States Patent Office Action for U.S. Appl. No. 11/890,760 dated Jul. 25, 2008 (8 pages).

United States Patent Office Action for U.S. Appl. No. 12/272,732 dated Apr. 26, 2011.

United States Patent Office Action for U.S. Appl. No. 12/272,732 dated Aug. 24, 2010.

United States Patent Office Action for U.S. Appl. No. 12/272,732 dated Dec. 9, 2011.

United States Patent Office Action for U.S. Appl. No. 12/272,732 dated Jul. 6, 2012 (12 pages).

United States Patent Notice of Allowance for U.S. Appl. No. 12/272,732 dated Aug. 9, 2013 (9 pages).

United States Patent Office Action for U.S. Appl. No. 12/442,135 dated May 16, 2012 (7 pages).

United States Patent Office Action for U.S. Appl. No. 12/442,135 dated Oct. 26, 2011 (7 pages).

United States Patent Office Action for U.S. Appl. No. 12/753,721 dated Dec. 12, 2011 (7 pages).

United States Patent Office Action for U.S. Appl. No. 12/753,721 dated May 9, 2013 (8 pages).

United States Patent Office Notice of Allowance for U.S. Appl. No. 11/890,760 dated Jan. 8, 2010 (6 pages).

(56) References Cited

OTHER PUBLICATIONS

United States Patent Office Notice of Allowance for U.S. Appl. No. 12/753,721 dated Aug. 3, 2012 (5 pages).
United States Patent Office Action for U.S. Appl. No. 14/206,796 dated Nov. 4, 2014 (35 pages).
United States Patent Office Action for U.S. Appl. No. 12/422,135 dated Dec. 17, 2014 (8 pages).
Dorwald, F.Z., Side Reactions in Organic Synthesis. A Guide to Succsesful Synthesis Design, Wiley-VCH Verlag GmbH & Co., Weinheim, Germany (2005) Preface.
International Search Report and Written Opinion for Application No. PCT/US2013/071520 dated Feb. 5, 2014 (12 pages).
International Search Report and Written Opinion for Application No. PCT/US2014/024785 dated Jul. 7, 2014 (13 pages).
United States Patent Office Action for U.S. Appl. No. 13/294,085 dated Oct. 3, 2014 (18 pages).
United States Patent Office Action for U.S. Appl. No. 13/452,560 dated Aug. 19, 2014 (10 pages).
United States Patent Office Action for U.S. Appl. No. 13/452,578 dated Sep. 23, 2014 (12 pages).
United States Patent Office Action for U.S. Appl. No. 14/150,633 dated Sep. 25, 2014 (12 pages).
United States Patent Office Action for U.S. Appl. No. 14/089,054 dated Aug. 15, 2014 (16 pages).
United States Patent Office Action for U.S. Appl. No. 14/205,627 dated Aug. 27, 2014 (25 pages).
United States Patent Office Action for U.S. Appl. No. 14/205,832 dated Aug. 27, 2014 (21 pages).
U.S. Appl. No. 14/089,054, filed Nov. 25, 2013, Presta

* cited by examiner

HYDROXYCARBOXYLIC ACIDS AND SALTS

CROSS-REFERENCE TO RELATED APPLICATIONS

This is a divisional of U.S. patent application Ser. No. 13/277,896, filed on Oct. 20, 2011, which is a divisional of U.S. patent application Ser. No. 12/422,135, filed Apr. 10, 2009, which is a continuation-in-part of U.S. patent application Ser. No. 11/890,760, filed Aug. 6, 2007, now U.S. Pat. No. 7,692,041, which claims priority to U.S. Provisional Patent Application No. 60/836,329, filed Aug. 7, 2006, the contents of all of which are herein fully incorporated by reference.

STATEMENT REGARDING FEDERALLY SPONSORED RESEARCH OR DEVELOPMENT

The invention was made with Government support under Grant No. 2003-364463-13003 and 2005-364463-15561 awarded by the USDA-CSRESS. The Government has certain rights in the invention.

REFERENCE TO SEQUENCE LISTING, A TABLE, OR A COMPUTER PROGRAM LISTING COMPACT DISC APPENDIX

Not applicable.

BACKGROUND OF THE INVENTION

This invention describes a method for synthesizing hydroxycarboxylic acid salts from polyols using nitric acid and oxygen as the oxidizing agents and applying the hydroxycarboxylic acid salts for uses that include corrosion inhibiting materials and components of concrete.

Hydroxycarboxylic acids and hydroxycarboxylic acid salts are well recognized as corrosion inhibitors particularly effective in inhibiting metal corrosion when the metal is in contact with water or an aqueous solution (U.S. Pat. No. 2,529,177; U.S. Pat. No. 2,529,178; Erasmus, 1971; Marukume, 1993; Hashimoto, 1976; and U.S. Pat. No. 4,120,655).

Nieland et al. taught that these hydroxycarboxylic acids, or salts thereof, may contain a single carboxylic acid function, as in the case of gluconic acid (U.S. Pat. No. 2,529,178), or multiple carboxylic acid functions as in the case of tartaric acid, a hydroxydicarboxylic acid, or citric acid, a hydroxytricarboxylic acid (U.S. Pat. No. 2,529,170). Nieland et al. have also taught that hydroxycarboxylic acids, or salts thereof, with multiple carboxylic acid functions, such as tartaric acid (U.S. Pat. No. 2,529,170), generally exhibit better corrosion inhibition properties than do comparable hydroxymonocarboxylic acids, such as gluconic acid (U.S. Pat. No. 2,529,178).

Hydroxycarboxylic acids have also been shown to inhibit metal corrosion in aqueous salt brine such as sea water (Mor, 1971; Mor 1976; and Wrubl, 1984) or formulated brine solutions (Kuczynski, 1979; Korzh, 1981; Sukhotin, 1982; and Abdallah, 1999), some employed for specific applications, such as in industrial cooling systems (Sukhotin, 1982).

Metal corrosion inhibitors are commonly mixtures of components that include hydroxycarboxylic acids, or salts thereof, the mixtures sometimes described as providing a synergistic or cooperative effect with components other than hydroxycarboxylic acids in corrosion inhibition rendering corrosion inhibition properties better than and/or different from the individual components.

Crambes et al. describe (U.S. Pat. No. 4,120,655) the use of hydroxycarboxylic acids selected from the group tartaric, citric and gluconic in addition to a phosphoric acid ester of an alkanolamine to inhibit the corrosion of ferrous metals in aqueous media including aqueous media with high salt content. Numerous additional examples of the use of hydroxycarboxylic acids or hydroxycarboxylic salts in mixtures with components other than hydroxycarboxylic acids that serve as corrosion inhibiting agents have been reported (U.S. Pat. Nos. 3,589,859; 3,711,246; 4,108,790; 5,891,225; 5,531,931; 5,330,683; and Foroulis, 1971; Foroulis, 1972; Foroulis, 1973; Hiroshige, 1973; and Birk, 1976).

Sufrin et al. (U.S. Pat. No. 5,330,683) claims use of gluconate, with additional components that include sorbitol or mannitol, as a corrosion inhibition agent in brine. However, it is clear from earlier reports (Mor, 1971; Mor 1976; Wrubl, 1984; and Kuczynsiki, 1979) that gluconate had been reported effective as a corrosion inhibitor in brine.

Hydroxycarboxylic acids or salts thereof have a documented, long history of use as corrosion inhibitors in liquid and solid media. They can function as corrosion inhibitors for metals in contact with water or aqueous solutions. They can serve as corrosion inhibitors in aqueous solutions that have low to high salt concentrations, wherein those salts include, but are not limited to alkali or alkaline metal salts of halides or other anionic components. They can function as corrosion inhibitors in the absence or presence of added substances. When they function as corrosion inhibitors in the presence of added substances the added substances may provide a positive synergistic corrosion inhibitory effect. Hydroxycarboxylic acids or salts forms with a single carboxylic acid function or multiple carboxylic acid functions can perform as corrosion inhibitors. Salt forms of these hydroxycarboxylic acids as corrosion inhibitors may have different cation components such as, but not limited to, alkali and alkaline earth cations. Hydroxycarboxylic acids or salt forms can serve as corrosion inhibitors against a number of metals, including, but not limited to iron, aluminum, copper and zinc. The hydroxycarboxylic acids or salt forms can serve as corrosion inhibitors in a multitude of applications where the use of nontoxic agents is an important advantage or requirement in the application, including but not limited to: cleaning of metal equipment; as corrosion inhibiting agents with corrosive salts, or other materials; for deicing purposes on surfaces in cold weather; in applications involving storage or transport of water or aqueous solutions in metal containers or conduits; in concrete and concrete containing metal components such as structural steel bars.

A need however remains for the availability of environmentally desirable materials for use as corrosion inhibiting agents for a variety of applications. Furthermore, it is clear that there is a need for such materials on a commercial scale for applications that include, but are not limited to, corrosion inhibiting agent in use with deicing agents for use on roadways and pedestrian walkways affected by snow and ice during cold weather periods, for use in concrete in contact with metal reinforcing bars, for cleaning boilers and other metal equipment. Materials that employ good corrosion inhibiting characteristics, are environmentally desirable, and can be produced economically on a large scale would be welcomed for commercial application on a large scale.

Hydroxycarboxylic acids and hydroxycarboxylic salts are also widely described as admixtures to concrete used to favorably influence different characteristics of concrete. Hydroxycarboxylic acids as admixtures (additives) to concrete formulations can serve to favorably effect how the concrete is applied and provide favorable characteristics of the concrete once it has hardened and is in use. Concrete admixtures include but are limited to roles as high-performance water reducers, improve concrete strength, and improve slump contraction (Wang, 2007). Such materials have been employed as set retarding additives (U.S. Published Patent Application No. US 2005-271431), as a set retarder for downhole use (Drochon, 2003), as components to aid in production of rapid setting cement (U.S. Published Patent Application No. 2002-228008), as components of aqueous cementing fluids to increase compression strength (U.S. Published Patent Application No. 2; 004-822459), as a setting controlling agent (e.g. tartaric acid, K Na tartrate, and trisodium citrate) for use in production of cement hardened body (Sakamoto, 2004), as a component of a blowing material for repairing degraded concrete (Araki, 2003), as a component of a plasticizer or superplasticizer in cement (Cerulli, 2002), as a component of a water-proof agent for concrete (Wu, 1999), as components of low-shrinkage cements useful for paving (Sekiguchi, 1993), as components of lightweight cellular cement articles (Sakurada, 1989), as a component of a rust-preventing composition in cement for steel reinforcement (Nakano, 1986), as components of refractory cements for use at high temperatures (Denki, 1985), as a component of rapidly hardening cement (Denki II, 1985), as a component for retarding the setting of cement mortars for large deep wells (Ene, 1982). The polyhydroxycarboxylic acids used as components of the setting retardants described in Ene were prepared by oxidation of molasses with nitric acid at 90° C. followed by neutralization.

Consequently, it is clear that there is a need for polyhydroxycarboxylic acids and their salts on a commercial scale for concrete production applications as illustrated herein and include but are not limited to those uses, as they reflect only a portion of the reported uses in conjunction with concrete. Such materials are also environmentally desirable in concrete and in related mortar applications, and their large scale economic production would be welcomed for commercial application on a large scale.

Salts of glucaric acid are also sold as food supplements. Monopotassium glucarate (potassium hydrogen glucarate) is used to maintain healthy cholesterol levels already within normal ranges, whereas calcium D-glucarate is used to promote glucuronidation, a process in which the body eliminates toxins and other adverse substances (U.S. Pat. Nos. 4,845,123; 5,561,160; and 5,364,644). Monopotassium glucarate has a relatively low water solubility (about 10%) and calcium D-glucarate is very insoluble in water. Therefore water soluble dipotassium D-glucarate hydrate (Styron, 2002) and monosodium monopotassium D-glucarate dihydrate (Styron, 2002) offer opportunities as food supplements and other applications where their water solubility is advantageous, and preferred over the less water soluble glucarate salts.

Given the long documented history of the effectiveness of hydroxycarboxylic acids as corrosion inhibitors and as components of cement and products therefrom, and their attraction as materials for safe use in the environment, it is desirable to have these materials available in large quantities for numerous applications. It is also desirable to be able to employ a single, basic technology to the oxidation of these varied polyols for the production of the desired hydroxycarboxylic acid salt products for use as corrosion inhibiting materials or concrete admixture materials. Furthermore, it is desirable to be able to apply the technology to a variety of polyol or carbohydrate feedstocks to produce oxidation products with attractive properties that extend beyond those cited here. The currently employed commercial methods of preparation of the common hydroxycarboxylic acids or salts thereof are principally biologically induced transformations or fermentations, as for example in the production of tartaric acid (U.S. Pat. No. 2,314,831), gluconic acid (U.S. Pat. No. 5,017,485), and citric acid (U.S. Pat. No. 3,652,396). The fermentation of suitable carbohydrate feedstocks for fermentation to the target acid requires specific microorganisms and special conditions to effect each of the fermentations, which are complex and multistep processes (Wisconsin Biorefiners).

All patents, patent applications, provisional patent applications and publications referred to or cited herein, are incorporated by reference in their entirety to the extent they are not inconsistent with the teachings of the specification.

BRIEF SUMMARY OF THE INVENTION

This invention describes novel chemical oxidation methods for polyols to prepare hydroxycarboxylic acids, as single oxidation products or in mixtures of oxidation products, applicable to commercial scale production. The invention also describes conversion of the oxidation products to mixtures of salt products or to individual salt products. The oxidation products can be used as corrosion inhibiting materials for a variety of corrosion inhibiting applications, as concrete admixtures, and for other applications that can take advantage of the properties of the product mixtures or pure organic compounds isolated from the mixtures. The preferred chemical oxidation method employs nitric acid as the oxidizing agent in aqueous solution. The oxidation method is applicable to polyols in general, of which carbohydrates provide multiple and diverse structurally different examples.

DETAILED DESCRIPTION OF THE INVENTION

This invention is directed to the chemical preparation of hydroxycarboxylic acids, as single oxidation products or as mixtures of oxidation products, applicable to commercial scale production, and employing the oxidation products as corrosion inhibiting materials for a variety of corrosion inhibiting applications, as components of concrete, and for any other applications that can take advantage of the availability of these oxidation products.

Hydroxycarboxylic acids can be considered as oxidation derivatives of carbohydrates or other polyols, a polyol meaning any organic compound with two or more alcohol hydroxyl groups. Such carbohydrates or polyols include, but are not limited to: simple aldoses and ketoses such as glucose, xylose or fructose; simple polyols such as glycerol, sorbitol or mannitol; reducing disaccharides such as maltose, lactose, or cellobiose; reducing oligosaccharides such as maltotriose, maltotetrose, or maltotetralose; nonreducing carbohydrates such as sucrose, trehalose and stachyose; mixtures of monosaccharides and oligosaccharides (that may include disaccharides); glucose syrups with different dextrose equivalent values; polysaccharides such as, but not limited to, starch, cellulose, arabinogalactans, xylans, mannans, fructans, hemicelluloses; mixtures of carbohydrates and other polyols that include one or more of the carbohydrates or polyols listed above.

The preferred chemical oxidation method employs nitric acid as the oxidizing agent in aqueous solution and has been described (U.S. Published Patent Application 2008/0033205). The nitric acid oxidation process described in Kiely and Hash (U.S. Published Patent Application 2008/0033205) has two main components; an oxidation process, followed by separation of nitric acid from organic products mixture, the organic procucts mixture being primarily composed of hydroxycarboxylic acids. The final organic products mixture can be further treated to generate an organic acids products mixture for use in acid forms or salt forms, or individual isolated hydroxyacid products for use in acid or salt forms.

Applying the nitric acid oxidation method (U.S. Published Patent Application 2008/0033205) to a glucose containing solution, produces a mixture of oxidation products that includes gluconic acid, glucaric acid, tartaric acid, tartronic acid, 5-ketogluconic acid, and glyceric acids, all of which are hydroxycarboxylic acids. It was anticipated that such a mixture, water soluble and in salt form, would have some effectiveness in iron corrosion inhibition tests. Employing standard iron corrosion inhibition testing as described here, it was determined that glucarate, from the hydroxydicarboxylic acid D-glucaric acid, was a more effective corrosion inhibiting agent than was gluconate, from the hydroxymonocarboxylic acid D-gluconic acid, as expected from the report of Neiland et al. (U.S. Pat. Nos. 2,529,177; and 2,529,178) that hydroxydicarboxylic acids display greater corrosion inhibiting characteristics than hydroxymonocarboxylic acids. When the complex oxidation product mixture in salt form was evaluated for corrosion inhibition performance, it was found surprisingly that the mixture was close in corrosion inhibition effectiveness to that of glucarate alone, and more effective than gluconate alone (Table 1). However, what was more surprising was that when a portion of the high valued glucarate had been removed from the oxidation mixture the effectiveness of the remaining product as a corrosion inhibitor was comparable to product mixture before the glucarate had been removed (Table 2). Since the dicarboxylic acid salt, such as a D-glucarate salt, is a more effective corrosion inhibitor than its corresponding monohydroxycarboxylic acid salt, a D-gluconate salt, it was fully expected that the material from which D-glucarate had been removed would be a less effective corrosion inhibitor than the material that still contained all of the glucarate. This finding adds economic value to the process since the high value D-glucaric salts can be removed from the oxidation leaving behind mixtures with corrosion inhibiting properties that are comparable to the mixtures with D-glucarate retained. The corrosion inhibiting effectiveness testing results (Table 1) also demonstrate that oxidation mixtures from structurally variable polyols also show good properties as corrosion inhibition agents. Thus, it has been determined that the chemical oxidation process gives rise to a complex product mixture, and that mixture can be used effectively as a corrosion inhibitor, with all of the higher valued D-glucarate in the mixture, or with some of the D-glucarate removed. Furthermore, it is clear that the nitric acid oxidation of the polyols using nitric acid as the oxidizing agent and reaction solvent, can successfully generate mixtures of oxidized organic acids, which in salt form, can be used directly as effective corrosion inhibiting agents without any need for purification beyond removal of the nitric acid as described (U.S. Published Patent Application 2008/0033205). The oxidative conversion of polyols to mixtures of hydroxycarboxylic acids with nitric acid offers for the first time a method for a rapid and effective large scale production method of these acids in salt form as cost effective and environmentally desirable corrosion inhibition agents and as beneficial cement components.

In addition to the oxidation product mixtures here described for use in corrosion inhibition applications, components of concrete and for other purposes, it is also desirable to use the oxidation process to prepare solid pure materials for particular or special applications that include, but are not limited to, corrosion inhibition in deicing applications such as when applied to surfaces for pedestrian or automotive use. It is desirable that such materials have, in addition to their corrosion inhibiting characteristics and environmentally favorable properties, crystalline properties, as opposed to being solid powders. Furthermore, it is advantageous that such materials be readily water soluble in order to perform well as corrosion inhibition materials in the presence of water and water and ice/snow. Crystalline materials mix well with solid deicers such as, but not limited to, sodium chloride or magnesium chloride, and allow for normal spreading of the solid deicer and crystalline corrosion inhibitor without concern for the corrosion inhibiting agent being blown about and not applied properly. Two such highly crystalline forms of glucarate which can be produced from the nitric acid oxidation method of glucose containing starting materials are dipotassium D-glucarate hydrate and monosodium monopotassium D-glucarate dihydrate, respectively (Styron, 2002). These materials have crystalline properties that make them very suitable for corrosion inhibition methods that employ solids, and in particular in combination with solid deicers. These materials are also readily soluble in water, making them very useful as corrosion inhibiting agents in aqueous solution.

Salts of glucaric acid are also sold as food supplements. The two widely sold salts of D-glucaric acid are monopotassium D-glucarate (potassium hydrogen D-glucarate) and calcium D-glucarate (U.S. Pat. Nos. 4,845,123; 5,561,160; and 5,364,644), respectively, the former to maintain healthy cholesterol levels already within normal ranges, and the latter to promote glucuronidation, a process in which the body eliminates toxins and other adverse substances. Monopotassium D-glucarate has a relatively low water solubility (about 10%), is a powdery substance, and solid calcium D-glucarate is very insoluble in water. Therefore nicely crystalline and water soluble dipotassium D-glucarate hydrate and monosodium monopotassium D-glucarate dihydrate (Styron, 2002), available from the oxidation process described here and potentially in large amounts as co-products of the even larger commercial oxidation mixtures products markets employing the mixtures in non-food applications, such as corrosion inhibiting agents and components of cement. Overall, these latter salts offer opportunities and advantages in whatever applications can use them as cost effective, water soluble hydroxyacids, and in some specific uses, e.g. food supplements, as water soluble D-glucaric acid salts.

Producing the mixtures of oxidized polyols employing the chemical oxidation process as described here has general advantages. These advantages include that the process is a simple process, with high recovery of products, that does not require a purification step to yield the product mixture useful for corrosion inhibition, concrete production, and other applications that can take advantage of the properties of the mixtures, beyond the easy removal of the nitric acid. Additionally, the same basic process can be employed for all of the desired oxidations employing suitable carbohydrates or other polyols. The same basic process is applicable to carbohydrates and other polyols in general, and can be generally used for oxidations of these feedstocks. The oxidation product mixture, in its salt form, can be used directly for corrosion inhibiting applications without costly need for further purification. The oxidation product mixture, in its salt form and/or acid form, can be used directly as a component of concrete without costly need for further purification. The oxidation product mixture, after removal of a higher valued pure product (or products), can be used for corrosion inhibiting applications. The oxidation product mixture, after removal of a higher valued pure product (or products), can be used for corrosion inhibiting applications. The oxidation product mixture, after removal of a higher valued pure product (or products), can be also be used as a component of concrete. A pure product isolated from the oxidation mixture can be used for corrosion inhibiting applications or different applications including as a food supplement. A number of renewable polyol or carbohydrate feedstocks can be employed as oxidation substrates to produce hydroxycarboxylic acid products with corrosion inhibiting characteristics. A number of renewable polyol or carbohydrate feedstocks can be employed as oxidation substrates to produce hydroxycarboxylic acid products for use as components of concrete. The oxidation products formed in these processes can be used for any number of applications requiring materials with environmentally desirable properties coupled with corrosion inhibiting properties. The oxidation products formed in these processes can be used for any number of applications requiring materials with environmentally desirable properties coupled with desirable properties as components of concrete preparations. The corrosion inhibiting applications include, but are not limited to: use in water systems with little to no additional dissolved substances; use in environments in contact with sea water for corrosion inhibiting applications; use in brine or water cooling applications; use in boiler and other metal equipment surface cleaning applications; use as corrosion inhibiting applications in brine solutions applied for deicing; use in oil well muds as corrosion inhibiting materials; use in cement and concrete as corrosion inhibiting materials. The availability of different mixtures as corrosion inhibiting agents or components of concrete opens up commercial potential for such mixtures as cost effective, environmentally favorable materials that can be readily and efficiently produced from renewable polyols and carbohydrates.

The following examples are offered to further illustrate but not limit both the compositions and the methods of the present invention. All percentages are by weight and all solvent mixture proportions are by volume unless otherwise noted.

Example 1

Corrosion Test Methods

Salt products prepared by the nitric acid oxidation methods and work up procedures described in this invention were evaluated for their corrosion inhibiting properties according to standard testing methods. Corrosion tests were performed according to the National Association of Corrosion Engineers (NACE) Standard TM0169-95 modified by the Pacific Northwest Snowfighters (PNS) (NACE TM0169-95).

The test procedure was modified to use 30 mL of a 3% solution of inhibitor per square inch of total coupon surface area. Stamped and numbered steel TSI coupons which met the ASTM F436 Type 1 requirement with a Rockwell hardness of C 38-45 were used for each corrosion test. Approximate coupon dimensions are 1.37 in. outer diameter, 0.60 in. inner diameter, and 0.10 in. thickness with a density of 7.85 grams per cubic centimeter. Coupons were placed in a sealed container on a rock tumbler with a non-abrasive cleanser for 30 minutes to remove surface grease and impurities. Coupons were wiped with acetone to remove any additional grease, rinsed with deionized water, and then acid etched with an 18.5% HCl solution for approximately 3 minutes. The coupons were rinsed with tap water, rinsed with deionized water, patted dry and placed in chloroform for 15 minutes. The coupons were removed from chloroform and allowed to air dry in a ventilated hood for 1 hour. Each coupon was then weighed to the nearest 0.1 mg. at least two times to ensure a consistent weight.

Distilled water was used to prepare each solution and control standard. Sodium chloride was used as the salt standard. A 3% solution of NaCl (EMD, analyzed reagent grade, 9.6 g) in distilled water (310.4 g) was prepared as a salt standard (w/v). Each test solution was prepared with 3% NaCl, 310.4 g distilled water, and a corrosion inhibitor. Two NaCl salt solutions containing each inhibitor were prepared at 3% and 1.5% inhibitor concentration (by weight of salt, 288 mg and 144 mg, respectively). Approximately 300 mL of each solution in distilled water was transferred to a clean 500 mL Erlenmeyer flask equipped with a rubber stopper which had been drilled to allow a thin line attached to a plastic rod to run through it. The pH of each solution was measured and recorded. Aqueous 5% sodium hydroxide was carefully added (1-2 drops) until a basic pH was established for each test solution. The pH of the NaCl and $H_2O$ control solutions was not altered. Three coupons were attached to a plastic bar suspended within each flask through the stopper hole. A timed device raised and lowered the test coupons so they were immersed in the test solution for 10 minutes of each hour for a 72 hour period. Tests were conducted at room temperature.

After the 72 h. test period, the coupons were quickly removed from solution, rinsed under tap water and vigorously rubbed to remove any surface corrosion material. The coupons were then placed in shallow evaporating dishes containing a cleaning solution of concentrated hydrochloric acid, stannous chloride (50 g/liter), and antimony chloride (20 g/liter) for 15 minutes. The coupons were removed from the acid solution, rinsed vigorously under tap water, and returned to the cleaning solution for an additional 15 minutes. The coupons were again removed from the acid solution, rinsed under tap water, rinsed under deionized water, patted dry, and placed in a vessel containing chloroform for 10 minutes. The coupons were removed from the chloroform and allowed to air dry under a ventilated hood for 1 hour before being weighed to the nearest 0.1 mg. Each coupon was weighed twice to ensure a true final weight. Corrosion rate in mils per year (MPY) was calculated from the measured weight loss of each coupon using the following equation:

$$MPY = \frac{\text{weight loss (mg)} \cdot 534}{\text{area (cm}^2\text{)} \cdot \text{time(h)} \cdot \text{metal density}}$$

metal density=7.85 g/cc
time=72 hours

The corrosion value for the control solution of distilled $H_2O$ was also calculated. The MPY value of the distilled water was subtracted from the MPY value of each sample solution containing 3% NaCl to provide a corrected MPY value, which is noted as MPY'. The MPY' values of each of three coupons in the test solution were averaged to determine the MPY' value of the entire test solution. A Percent Effectiveness value, which measures the rate of corrosion of sample as compared to the corrosion value for salt, was determined. The Percent Effectiveness of each solution is calculated as follows:

Percent Effectiveness =

$$\frac{(MPY \text{ of inhibitor sample} - MPY \text{ of } H_2O)}{(MPY \text{ of NaCl} - MPY \text{ of } H_2O)} \cdot 100 \text{ or}$$

$$\text{Percent Effectiveness} = \frac{MPY^1 \text{ of inhibitor sample}}{MPY^1 \text{ of NaCl}} \cdot 100$$

Accordingly, the distilled $H_2O$ control has a Percent Effectiveness value of 0%, while the 3% NaCl control has a 100% Percent Effectiveness value. The corrosion inhibitor samples have Percent Effectiveness values between 0% and 100%. In order for a material to be acceptable as a corrosion inhibitor, the Percent Effectiveness of the material must have a value of 30% or less as defined by PNS.

Table 1 shows corrosion rates (MPY), corrected corrosion rates ($MPY^1$), and percent effectiveness of water, 3% NaCl solution, and 3% NaCl solutions containing corrosion inhibitors derived from salts of hydroxycarboxylic acids. Each sample was dissolved in distilled water and the sample solution was made basic (>pH 8) with the exception of sodium D-gluconate and commercial liquid sodium gluconate product tested at their natural pH values of 6.1 and 3.2, respectively.

TABLE 1

Corrosion Rates (MPY), Corrected Corrosion Rates (MPY¹), and Percent Effectiveness of Corrosion Inhibitors in 3% NaCl Solutions*

| Corrosion Inhibitor | Inhibitor Concentration (%)* | MPY | MPY¹ | Percent Effectiveness |
|---|---|---|---|---|
| None (H₂O control) | 0 | 5.650 | 0.000 | 0.00% |
| sodium D-gluconate | 1.5 | 24.596 | 20.313 | 36.98% |
| sodium D-gluconate | 3.0 | 22.786 | 18.503 | 33.45% |
| commercial liquid gluconate product | 3.0 | 34.580 | 28.928 | 67.63% |
| sodium potassium D-glucarate | 1.5 | 23.726 | 19.443 | 35.28% |
| sodium potassium D-glucarate | 3.0 | 20.939 | 16.656 | 29.84% |
| nitric acid oxidized 95-99% liquid dextrose | 1.5 | 24.871 | 20.588 | 37.52% |
| nitric acid oxidized 95-99% liquid dextrose | 3.0 | 21.424 | 15.774 | 30.78% |
| nitric acid oxidized 41-44% liquid dextrose | 1.5 | 34.666 | 29.016 | 56.63% |
| nitric acid oxidized 41-44% liquid dextrose | 3.0 | 29.904 | 24.254 | 47.34% |
| nitric acid oxidized sucrose | 3.0 | 21.642 | 15.992 | 31.21% |
| None (NaCl control) | 0 | 57.574 | 51.235 | 100.00% |

*Concentrations are given in weight %.

Table 2 shows corrosion rates (MPY), corrected corrosion rates (MPY¹), and percent effectiveness of water, 3% NaCl solution, and 3% NaCl solutions containing corrosion inhibitors derived from nitric acid oxidized 95-99% liquid dextrose and nitric acid oxidized 95-99% liquid dextrose from which some D-glucarate has been removed. Each sample was dissolved in distilled water and the sample solution was made basic (>pH 8).

TABLE 2

Corrosion Rates (MPY), Corrected Corrosion Rates (MPY¹), and Percent Effectiveness of Nitric Acid Oxidized 95-99% Liquid Dextrose and Nitric Acid Oxidized 95-99% Liquid Dextrose with Less D-Glucarate as Corrosion Inhibitors in 3% NaCl Solutions*

| Corrosion Inhibitor | Inhibitor Concentration (%)* | MPY | MPY¹ | Percent Effectiveness |
|---|---|---|---|---|
| H₂O (control) | 0.00 | 5.027 | 0.000 | 0.00% |
| nitric acid oxidized 95-99% liquid dextrose | 3.25 | 19.464 | 14.434 | 24.03% |
| nitric acid oxidized 95-99% liquid dextrose less D-glucarate | 3.25 | 15.833 | 10.807 | 17.99% |
| nitric acid oxidized 95-99% liquid dextrose | 3.90 | 17.149 | 12.122 | 20.18% |
| nitric acid oxidized 95-99% liquid dextrose less D-glucarate | 3.90 | 14.568 | 9.542 | 15.88% |
| nitric acid oxidized 95-99% liquid dextrose | 4.55 | 16.041 | 11.013 | 18.33% |
| nitric acid oxidized 95-99% liquid dextrose less D-glucarate | 4.55 | 15.516 | 10.489 | 17.46% |
| NaCl (control) | 0.00 | 67.238 | 62.211 | 100.0% |

*Concentrations are given in weight %.

It is clear from the results provided in Tables 1 that by increasing the concentration of corrosion inhibitor in 3.0% sodium chloride solution there is a marked improvement (lowering) of the percent effectiveness (PNS score). It is also clear that the nitric acid oxidation product from the oxidized 95-99% liquid dextrose product performs close to that of a pure form of glucarate and better than gluconate, with the former two materials at about the preferred 30% effectiveness value and gluconate at a higher value. The commercial liquid gluconate product showed a very high (poor performance) corrosion effectiveness score of greater than 60%. The glucarate and oxidized dextrose materials were adjusted to a higher pH than gluconate and commercial liquid gluconate because the former materials have significantly higher water solubility (ca. 70%) than the gluconate product (ca. 60%) at the higher pH, and can be transported and used at the higher pH value and the correspondingly higher concentration than can gluconate.

It has been demonstrated here, and in earlier reports, that a dihydroxyacid such as D-glucaric acid is a better corrosion inhibiting agent than the corresponding monohydroxyacid, e.g., D-gluconic acid. Consequently, it was anticipated that when the nitric acid oxidized 95-99% liquid dextrose product used in the corrosion rate tests had some of the glucarate removed from this oxidation mixture, the resulting material would be a less effective corrosion inhibiting material than the material that still contained all of the glucarate. Surprisingly, contrary to this obvious expectation, the nitric acid oxidized 95-99% liquid dextrose less glucarate samples were comparable as corrosion inhibiting materials to those from nitric acid oxidized 95-99% liquid dextrose with no glucarate removed (Table 2). This unexpected result further raises the value of the overall oxidation process described here, because some high value D-glucaric acid can first be removed from the oxidation product mixture, leaving a product mixture that has good corrosion inhibiting properties.

Consequently, the oxidized products described in this invention offer several advantages over single hydroxyacids as corrosion inhibitors that include, but are not limited to: 1) they have very high water solubilities which allows for lowered cost of transport and use; 2) they have significantly enhanced performance at pH values above 7 which decreases the amount of material that is used in a corrosion inhibiting application and lowers the cost of that use; 3) they do not require purification to single materials to effectively inhibit corrosion, an important production cost lowering factor in their production, 4) some high value D-glucaric acid can be easily separated from the oxidation mixture of glucose based substrates, leaving a product behind that offers corrosion inhibiting properties that are comparable to the mixture that contained all of the glucaric acid.

Example 2

Samples Prepared as Concrete Admixtures

The samples prepared as concrete admixtures were of the type listed in Table 2 Sample I being oxidation mixtures as described with no glucarate removed, Sample II being oxidation mixtures as described with some glucarate removed, and Sample III being a single admixture substance from the oxidation, i.e., monopotassium D-glucarate.

I nitric acid oxidized 95-99% liquid dextrose
II nitric acid oxidized 95-99% liquid less D-glucarate
III monopotassium D-glucarate A pH greater than 9 was established for Samples I-II by addition of sodium hydroxide, whereas the pH of the Sample III solution was established as greater than 9 by addition of potassium hydroxide.

A.—Admixture Sample Preparation.

Numerous samples were prepared from the dextrose oxidation product to be tested as potential concrete admixtures. Each sample was varied by control of reaction conditions, work-up procedure and product analysis by ion chromatography for D-glucarate, D-gluconate, nitrate and additional organic acids in the final product. Whole product samples (I), whole product with some D-glucarate removed (II), and single product glucarate (III) were prepared and submitted for admixture analysis. All samples were tested and analyzed by TEC Services: Testing, Engineering and Consulting Services, Inc., 235 Buford Dr., Lawrenceville, Ga. 30045.

B.—Concrete Admixture Test Methods.

Salt products prepared by the nitric acid oxidation methods and work up procedures described in this invention were evaluated for their concrete admixture properties according to standard testing methods. Admixture tests were performed according to ASTM Standard C494/C494 M-05a, 2005 "Standard Specifications for Chemical Admixtures for Concrete", ASTM International, West Conshohocken, Pa., 2005.

C.—Analysis of Admixtures.

Standard concrete mixtures of cement, water, rock, sand, and air entraining agent were prepared for laboratory testing of concrete admixtures. Approximately 4 L of each sample were prepared at 20% concentration of solids after being made basic with sodium hydroxide and submitted for admixture analysis. The mono potassium D-glucarate product was prepared at 10% solids after being made basic with potassium hydroxide. Each sample was added to a standard concrete mixture and tested for performance and efficiency as a concrete admixture as defined by the ASTM Standard C494/C494 M-05a. The following physical requirements were measured for each admixture: water content, slump, percent air, weight, time of initial and final set, and compressive strength. A concrete sample without the addition of an admixture was established as a control sample. Each admixture sample was added to separate concrete test mixtures and measured against the control. One control mixture and one trial mixture containing each of the admixtures was prepared and tested for fresh and hardened concrete properties. Samples were classified as admixture types as defined by ASTM C494 standards. There are eight types of admixtures: Type A (water reducing), Type B (set retarding), Type C (accelerating), Type D (water reducing/set retarding), Type E (water reducing/accelerating), Type F (high range water reducing), Type G (high range water reducing/set retarding), and Type H (mid-range water reducing). Admixture samples were added to the concrete test mixtures in optimal doses to meet the physical requirements of Type A and Type D admixtures. Samples I-III were also tested as potential Type A admixtures.

Type A admixtures maximize the benefits of increased hydration in hardened and plastic concrete (Collepardi, 1995). The specifications for Type A water reducing admixtures, as well as the testing results from Samples I-III are presented in Table 3. As defined in Section 3 of ASTM C494/C494-05a, Type A admixtures must reduce the quantity of mixing water required to produce concrete of given consistency by 5-12% and stay within a defined time of set comparable to the control, unlike Type D water reducers/set retarders. Sample I-III were all dosed at approximately 2.5 oz/cwt cement; however, due the higher concentrations of Samples I and II, the effective dose (solid admixture amount) was almost twice the amount of Sample III. While all Samples meet water reduction, time of set, and compressive strength standards for Type A water reducers, the higher effective doses of Samples I and II appear to give better performance as evidenced by the higher percent of water reduction.

Type D admixtures encompass the properties of both a set retarder and a water reducer. To meet specifications, Type D admixtures must increase the time of set up to 3.5 h and reduce the amount of requisite mixing water up to 12%. As specified in Table 4, Type D admixtures must meet the compressive strength requirements of at least 110% of the concrete control. The specifications for Type D (water reducing/set retarding) admixtures, as well as the testing results from Samples I-III are presented in Table 4. Dosage amounts of any admixture are relative to the amount of cement in the entire concrete mixture. For example, Sample I was dosed at 2.9 oz/cwt cement in order to meet the ASTM requirements for a Type D admixture as opposed to the 2.4 oz/cwt required to meet Type A specifications (Table 3). This minor increase in dosage is significant in defining and applying Sample I as either a Type D or a Type A admixture. In addition to increasing the set times, water reduction was also increased at a higher dose of Sample I. Samples II and III also met Type D admixture standards at higher doses of 4.0-5.0 oz/cwt cement. Samples I-III meet compressive strength and durability standards over time. As Type D admixtures, Samples I-III improve the hardened properties of concrete and ensure even set. Type D admixtures are essential in warmer climates, ensuring lengthened time of set and improved workability while conserving water. Table 4 demonstrates the effectiveness of Samples I-III as Type D admixtures. Clearly, changing the dosage of admixtures of Samples I-III, and other samples of hydroxycarboxylic acids produced using the oxidation process described here employing a range of process conditions and from different polyols, underscores the versatility of such oxidation products as useful for different admixture types.

In summary, the testing results presented in Tables 3 and 4 illustrate the versatility and effectiveness of products from oxidation of a polyol with nitric acid as concrete admixtures. As illustration, Samples I and II are applied at lower concentrations of solids than most admixtures currently on the market (Collepardi, 1995).

TABLE 3

Mix Proportions and Test Results for Dextrose Oxidation Products as Type A (water reducing) Admixtures

| Admixture (Concentration) | Control (0%) | I (20%) | II (20%) | III (10%) | Type A Specifications (ASTM C494) |
|---|---|---|---|---|---|
| Cement (lbs/cu yd) | 517 | 517 | 517 | 517 | 512-521 |
| Water (lbs/cu yd) | 287.5 | 270 | 265 | 273 | ≤95% of control |
| Air Entrainment (oz/cwt) | 0.58 | 0.41 | 0.39 | 0.40 | |
| Admixture Dose (oz/cwt) | 0.0 | 2.4 | 2.4 | 2.5 | |
| Solid Admixture Amt (oz) | 0.0 | 0.48 | 0.48 | 0.25 | |
| Glucarate Concentration (% of solid) | 0.0 | 40 | 35 | 100 | |
| Nitrate Concentration (% of solid) | 0.0 | 6 | 4 | 0.0 | |
| Water reduction (% of control) | 0.0 | 6.00 | 7.58 | 5.04 | ≥5.0% |
| Slump (in.) | 3.50 | 3.00 | 3.00 | 3.00 | 3"-4" |
| Air (%) | 5.50 | 5.50 | 5.00 | 5.50 | 5-7 (±0.5 of control) |
| Initial Set Time Difference | 0.00 | 1:13 later | 1:02 later | 0:47 later | 1:00 earlier-1:30 later |
| Final Set Time Difference | 0.00 | 1:28 later | 1:09 later | 0:57 later | 1:00 earlier-1:30 later |
| Compressive Strength psi (% of control) | | | | | |
| 7 days | 3150 | 3650 (116%) | NA | 3930 (125%) | 110% |

TABLE 4

Mix Proportions and Test Results for Dextrose Oxidation Products as Type D (water reducing/set retarding) Admixtures

| Admixture (Concentration) | Control (0%) | I (20%) | II (20%) | III (10%) | Type D Specifications (ASTM C494) |
|---|---|---|---|---|---|
| Cement (lbs/cu yd) | 517 | 517 | 517 | 517 | 512-521 |
| Water (lbs/cu yd) | 287.5 | 264 | 273 | 273 | ≤95% of control |
| Air Entrainment (oz/cwt) | 0.58 | 0.39 | 0.32 | 0.34 | |
| Admixture Dose (oz/cwt) | 0 | 2.9 | 5.0 | 4.8 | |
| Solid Admixture Amt (oz) | 0 | 0.58 | 1 | 0.48 | |
| Glucarate Concentration (% of solid) | 0 | 40% | 28% | 100% | |
| Nitrate Concentration (% of solid) | 0 | 6% | 5% | 0% | |
| Water reduction (% of control) | 0.0 | 8.10 | 5.04 | 5.04 | ≥5.0% |
| Slump (in.) | 3.5 | 3.0 | 3.5 | 3.5 | 3"-4" |
| Initial Set Time Difference | 0.00 | 1:30 later | 2:36 later | 1:27 later | 1:00-3:30 later |
| Final Set Time Difference | 0.00 | 1:46 later | 2:43 later | 2:06 later | 1:00-3:30 later |
| Compressive Strength, psi (% of control) | | | | | |
| 7 days | 3150 | NA | 3980 (126%) | 3690 (117%) | 110% |
| 28 days | 4290 | | 5530 (129%) | 5080 (118%) | 110% |

Example 3

General Methods

Solutions were concentrated in vacuo (15-25 mbar) using a rotary evaporator and water bath at 50° C. pH measurements were made with a Thermo Orion 310 pH meter (Thermo Fisher Scientific, Inc., Waltham, Mass., USA) which was calibrated prior to use. Oxidations were carried out in Mettler Toledo LabMax reactor, designed to operate as a computer controlled closed-system reactor. The Labmax was fitted with a top-loading balance, a liquid feed pump, an oxygen Sierra flow valve, a mechanically driven stirring rod, a thermometer, a 2 liter thermal jacketed flask, an FTS recirculating chiller, a pressure manifold fitted with pressure relief valves and pressure gauge, and a personal computer with CamileTG v1.2 software. The software installed allows the operator to program experiments based on specific parameters and conditions. Oxidation procedures are readily changed as needed as illustrated in Examples 9-13.

Examples of, but not limited to, preparation of polyol aqueous solutions suitable for nitric acid oxidation.

Example 4

D-Glucose Solution Preparation

Aqueous 62.3% D-glucose solution used in the oxidations was prepared by adding solid D-glucose (325.0 g, 1.50 mol) to 195.0 grams of deionized water in a screw-capped flask containing a stir bar. Prior to adding solid D-glucose to the water, the water was heated to ca. 60° C. with stirring. Once the D-glucose was dissolved, the solution was allowed to cool to ambient temperature and dry sodium nitrite (1.20 g) was added. The total weight of the solution was 521.5 g.

Example 5

Liquid Dextrose Solution (95-99% Dextrose Equivalent) Preparation

Aqueous 62.3% liquid dextrose (95-99% dextrose equivalent) solution used in the oxidation was prepared by adding semi-solid liquid dextrose, StaleyDex® 95 Liquid Dextrose (457.8 g, dry substance 71.0%) to 62.25 grams of deionized water in a screw-capped flask containing a stir bar. The flask and its contents were heated to ca. 60° C. to dissolve the semi-solid liquid dextrose. Once the liquid dextrose was dissolved, the solution was allowed to cool to ambient temperature and dry sodium nitrite (1.20 g) was added. The total weight of the solution was 521.5 g.

Example 6

Lower Dextrose Equivalent (41-45%) Corn Syrup Solution Preparation

Aqueous 62.3% liquid corn syrup used in the oxidation was prepared by adding viscous corn syrup 41-45% dextrose equivalent, Staley®1300 Corn Syrup (404.9 g, dry substance 80.3%) to 115.2 grams of deionized water in a screw-capped flask containing a stir bar. The flask and its contents were heated to ca. 60° C. to dissolve the viscous corn syrup. Once dissolved, the solution was allowed to cool to ambient temperature and dry sodium nitrite (1.20 g) was added. The total weight of the solution was 521.3 g.

Example 7

Preparation of a Nitric Acid Hydrolyzed Starch Mixture for Direct Nitric Acid Oxidation Aqueous 50% hydrolyzed starch mixture was prepared by adding corn starch (50.0 g) in portions (5.0 g) over a 2.25 h period to 35% nitric acid (50.0 g) at 65° C. The mixture was suitable for direct nitric acid oxidation as described in Examples 9-13.

Example 8

Sucrose Solution Preparation

The aqueous 62.3% sucrose solution used in the oxidations was prepared by adding solid sucrose (308.0 g, 0.75 mol) to 184.9 grams of deionized water in a screw-capped flask containing a stir bar. Prior to adding solid sucrose to the water, the water was heated to ca. 60° C. with stirring. Once the sucrose was dissolved, the solution was allowed to cool to ambient temperature and dry sodium nitrite (1.20 g) was added. The total weight of the solution was 494.0 g.

Examples of, but not limited to, nitric acid oxidation of polyol procedures

Example 9

Oxidation Procedure: 1:4 Polyol to Nitric Acid Molar Ratio

The Recipe Menu was accessed using the Labmax Camille TG v1.2 software. Stage 1—the temperature was set at 25° C.; the stirring rod speed set at 200 rpm (and held constant throughout all remaining stages); time set for 1 minute duration. Stage 2—the temperature was set at 25° C., and the pressure set at 0.25 bar, time set for 3 minutes. Stage 3—the temperature was set at 25° C., and the pressure set at 0.25 bar above atmosphere, and 43.3 grams of a 62.3% (w/w) D-glucose solution, containing 0.23% by weight of sodium nitrite, set to be added over 30 minutes. Stage 4—the temperature was set at 25° C., and the pressure maintained at 0.25 bar, and the duration was set at 10 minutes. Stage 5—the temperature was set at 25° C., and the pressure maintained at 0.25 bar, and 172.9 grams of a 62.3% (w/w) D-glucose solution, containing 0.23% by weight of sodium nitrite was set to be added over 90 minutes. Stage 6—the temperature was set at 25° C., and pressure maintained at 0.25 bar, time set for 5 minutes. Stage 7—the temperature was increased to 30° C., and the pressure was increased to 0.50 bar, and the time set to 60 minutes duration. Stage 8—the temperature was set at 30° C., and the pressure maintained at 0.50 bar, and time was set for over 90 minutes. Stage 9—the reactor temperature was set to cool to 25° C. over 10 minutes. Once the reaction was programmed to proceed as indicated, nitric acid (68-70%, 187 mL, ca. 3.0 mol) was added to the reactor. The reaction recipe was initiated and starting at stage 1, the reactor was closed to the atmosphere. When the reaction had progressed through all of the stages, the reaction mixture was removed from the reactor through the bottom valve of the reactor.

Example 10

Oxidation Procedure: 1:3 Polyol (D-Glucose) to Nitric Acid Molar Ratio

The Recipe Menu was accessed using the Labmax Camille TG v1.2 software. Stage 1—the temperature was set for 25° C. (and held constant throughout all remaining stages) and the stirring rod speed set at 200 rpm (and held constant throughout all remaining stages); 282 mL (68-70%, 4.5 mol) nitric acid was added to the reactor through a top port; time was set for 1 minute duration. Stage 2—the pressure was set at 0.25 bar above atmosphere, time set for 3 minutes duration (and held constant throughout all remaining stages). Stage 3—added to the nitric acid was 86.6 grams of a 62.3% (w/w) D-glucose solution containing 0.23% by weight of sodium nitrite, set to be added over 30 minutes. Stage 4—temperature and pressure held constant for a duration of 10 minutes. Stage 5—added to the nitric acid was 345.8 grams of a 62.3% (w/w) D-glucose solution containing 0.23% by weight of sodium nitrite, set for a duration of 90 minutes. Stage 6—temperature and pressure held constant for a duration of 20 minutes. Once the reaction was programmed to proceed as indicated the reaction recipe was initiated and starting at stage 1, the reactor was closed to the atmosphere. When the reaction had progressed through all of the stages, the reaction mixture was removed from the reactor through the bottom valve of the reactor.

Example 11

Oxidation Procedure 1:3 Polyol (95-99% Dextrose Equivalent, Liquid Dextrose Solution) to Nitric Acid Molar Ratio The Recipe Menu was accessed using the Labmax Camille TG v1.2 software. Stage 1—the temperature was set for 25° C. (and held constant throughout all remaining stages) and the stirring rod speed was set at 200 rpm (and held constant throughout all remaining stages); 282 mL (68-70%, 4.5 mol) nitric acid was added to the reactor through a top port; time was set for 1 minute duration. Stage 2—the pressure was set at 0.25 bar above atmosphere, time set for 3 minutes duration (and held constant throughout all remaining stages). Stage 3—added to the nitric acid was 86.6 grams of a 62.3% (w/w) liquid dextrose solution, StaleyDex®95 solution, containing 0.23% by weight of sodium nitrite, set to be added over 30 minutes. Stage 4—temperature and pressure held constant for a duration of 10 minutes. Stage 5—added to the nitric acid was 345.8 grams of a 62.3% (w/w) liquid dextrose solution, StaleyDex®95, containing 0.23% by weight of sodium nitrite, set for a duration of 90 minutes. Stage 6—temperature and pressure held constant for a duration of 20 minutes. Once the reaction was programmed to proceed as indicated the reaction recipe was initiated and starting at stage 1, the reactor was closed to the atmosphere. When the reaction had progressed through all of the stages, the reaction mixture was removed from the reactor through the bottom valve of the reactor.

Example 12

Oxidation Procedure 1:3 Polyol (41-45% Dextrose Equivalent Corn Syrup Solution) to Nitric Acid Molar Ratio The Recipe Menu was accessed using the Labmax Camille TG v1.2 software. Stage 1—the temperature was set for 30° C. (and held constant throughout all remaining stages) and the stirring rod speed was set at 200 rpm (and held constant throughout all remaining stages); 282 ml (68-70%, 4.5 mol) nitric acid was added to the reactor through a top port; time was set for 1 minute duration. Stage 2—the pressure was set at 0.25 bar above atmosphere, time set for 3 minutes duration (and held constant throughout all remaining stages). Stage 3—added to the nitric acid was 86.6 grams of a 62.3% (w/w) solution of 41-45% dextrose equivalent corn syrup, Staley®1300, solution containing 0.23% by weight of sodium nitrite, set to be added over 30 minutes. Stage 4—temperature and pressure held constant for a duration of 10 minutes. Stage 5—added to the nitric acid was 345.8 grams of a 62.3% (w/w)) solution of 41-45% dextrose equivalent corn syrup, Staley®1300, solution containing 0.23% by weight of sodium nitrite, set for a duration of 90 minutes. Stage 6—temperature and pressure held constant for a duration of 20 minutes. Once the reaction was programmed to proceed as indicated the reaction recipe was initiated and starting at stage 1, the reactor was closed to the atmosphere. When the reaction had progressed through all of the stages, the reaction mixture was removed from the reactor through the bottom valve of the reactor.

Example 13

Oxidation Procedure 1:6 Polyol (Sucrose) to Nitric Acid Molar Ratio

The Recipe Menu was accessed using the Labmax Camille TG v1.2 software. Stage 1—the temperature was set for 35° C. and the stirring rod speed was 200 rpm (and held constant throughout all remaining stages); 312.5 ml (68-70%, 5.0 mol) nitric acid was added to the reactor through a top port; time was set for 1 minute duration. Stage 2—temperature was set at 35° C., the pressure was set at 0.25 bar above atmosphere (and held constant throughout all remaining stages), time set for 3 minutes duration. Stage 3—temperature was set at 35° C., added to the nitric acid was 82.2 grams of a 62.3% (w/w) sucrose solution containing 0.23% by weight of sodium nitrite, set to be added over 30 minutes. Stage 4—temperature was set at 35° C. and time was set for 10 minutes duration. Stage 5—temperature was set at 35° C., added to the nitric acid was 328.6 grams of a 62.3% (w/w) sucrose solution, set for a duration of 90 minutes. Stage 6—temperature was set at 35° C. and duration was set for 5 minutes. Stage 7—temperature was increased to 40° C. for a duration of 15 minutes. Stage 8—temperature was set at 40° C. and the time was set for a duration of 20 minutes. Stage 9—the reaction was allowed to cool to 25° C. for a duration of 10 minutes. Once the reaction was programmed to proceed as indicated the reaction recipe was initiated and starting at stage 1, the reactor was closed to the atmosphere. When the reaction had progressed through all of the stages, the reaction mixture was removed from the reactor through the bottom valve of the reactor.

Examples of, but not limited to, different work up procedures for removal of nitric acid from a reaction mixture.

Example 14

Nitric Acid Removal

In this work up procedure, the Mech-Chem Diffusion Dialysis Acid Purification System laboratory scale Model AP-L05 was used to separate the nitric acid from organic product components in the reaction mixture (e.g., from Example 9). The Mech-Chem system contains two metering pumps, the first being the acid reclaim pump and the second being the acid reject pump. The acid reject pump was set at 30% (pump length) and 30% (pump speed) and the acid reclaim pump was set at 40% (pump length) and 40% (pump speed). This put the reclaim to acid reject ratio at about 1.2. The system was first primed with RO (reverse osmosis) water according to a standard setup procedure and then the water was removed from the acid tank in the unit. The acid tank was then filled with the diluted aqueous oxidation mixture and the water tank in the unit was filled with RO water. The acid purification unit was turned on with the pumps set as indicated and the process initiated. Over time, the diluted reaction mixture was separated into two distinct streams, the acid recovery stream and the product recovery stream.

Example 15

Nitric Acid Removal

In this work up procedure, the reaction mixture (e.g., from Example 10) was concentrated at reduced pressure (rotary evaporator). The first fraction distilled at ca. 23-34° C. and 50-120 millibar of pressure and contained NOX gases as evidenced from the brown color of nitrogen dioxide gas. The NOX gases were collected using a gas trap cooled with liquid nitrogen. The concentration of the reaction mixture continued until a viscous syrup remained. The liquid distillate was weighed (ca. 390 g on average) and the same amount, ca. 390 g of deionized water was added to the viscous syrup mother liquor. Further separation of nitric acid from the organic product was carried out employing diffusion dialysis. The Mech-Chem Diffusion Dialysis Acid Purification System laboratory scale model AP-105 was used to separate nitric acid form the organic product. The same conditions as described above in Example 14 were employed. Oxidation of liquid sugar solution as described above was repeated several times, each reaction mixture was mixed together with an average overall weight of 2.279 kg. Over a period of 24 hours of processing, the entire oxidation mixture solution had been collected in either the acid recovery stream or the product recovery stream.

Examples of, but not limited to, isolation procedures for salt products from nitric acid oxidations of polyols illustrated in examples 9-13 and work up procedures as illustrated in examples 14-15.

Example 16

Isolation of Combined Oxidation Products as Sodium Salts from Nitric Acid Oxidation Example 11, and Work up Procedure Example 15

The oxidation procedure described in Example 11 was carried out three times and the combined oxidation mixtures subjected to diffusion dialysis as illustrated in Example 15. Total amounts for the combined oxidation reactions: Staley Dex 95-810.72 g, 4.500 mol (based upon 100% dextrose); HNO$_3$—846 mL, 13.5 mol. Upon completion of the diffusion dialysis, the organic acid solution was diluted to a total volume of 3.3 L, the reclaimed nitric acid solution was concentrated to a total volume of 190 mL. These were labeled as organic acid stock solution and reclaimed nitric acid stock solution. Organic acid stock solution (300 mL) was chilled in an ice bath and titrated to a pH of 10 with aqueous NaOH (20 mL, 45% w/w). The solution, which became dark yellow, was allowed to warm to room temperature. The pH of the solution dropped over time but was maintained above 9 with additional NaOH (ca. 1 mL). The resulting solution was refrigerated overnight resulting in a final pH of 8.3. The solution was concentrated using a rotary evaporator and dried under reduced pressure for 48 h to give a tan, amorphous solid. The basification procedure was carried out in triplicate. The average dried weight of solid product was 66.4 g±1.45 g. Using this average value, the weight of the crude solid sodium salts for the total organic acid solution was calculated to be 730.4 g, 90.1% yield by weight.

Example 17

Alcohol Precipitation of Combined Oxidation Products as Sodium Salts from Nitric Acid Oxidation Example 11, and Work up Procedure Example 15

A portion of dried crude solid sodium salt mixture (tan amorphous solid, ca. 5.0 g) from Example 16 was dissolved in water (5 mL) to form a viscous amber solution. solution. Methanol (50 mL) was added to the solution and a tacky solid formed immediately. The mixture was stirred overnight without change in the appearance of the composition. The solution was decanted from the solid, and the solid was washed with methanol (3×10 mL) and dried under reduced pressure. The filtrate and washings were combined, concentrated using a rotary evaporator, and dried under reduced pressure. The precipitation procedure was carried out in triplicate (17a-c, Table 5).

TABLE 5

| Sample | Initial Solid Weight (g) | Precipitate Weight (g) | Dried Filtrate Weight (g) | Recovered Solid Weight (g) |
|--------|--------------------------|------------------------|---------------------------|----------------------------|
| 17a    | 5.0063                   | 4.6326                 | 0.5088                    | 5.1414                     |
| 17b    | 5.0047                   | 4.6438                 | 0.5422                    | 5.1860                     |
| 17c    | 5.0018                   | 4.6379                 | 0.5500                    | 5.1879                     |

Example 18

Isolation of Combined Oxidation Products as Sodium Salts from Nitric Acid Oxidation Example 12, and Work up Procedure Example 15

The oxidation procedure described in Example 12 was carried out three times and the combined oxidation mixtures subjected to diffusion dialysis as illustrated in Example 15. Total amounts for the combined oxidation reactions: Staley 1300-810.72 g, 4.500 mol (based upon 100% dextrose), HNO$_3$—846 mL, 13.5 mol. Upon completion of the diffusion dialysis, the organic acid solution was diluted to a total volume of 2.640 mL. The streams from diffusion dialysis were labeled as organic acid stock solution and reclaimed nitric acid stock solution. Organic acid stock solution (300 mL, pH 1.2) was chilled in an ice bath and titrated to a pH above 10 with aqueous NaOH (14 mL, 45% w/w). The solution, which became dark yellow, was allowed to warm to room temperature. The pH of the solution dropped over time but was maintained above 9 with additional NaOH (ca. 1 mL). The solution was cooled overnight resulting in a pH of 8. The solution pH was raised to above 9 with NaOH, and the solution was concentrated using a rotary evaporator and then dried under reduced pressure for 48 h to give a golden, amorphous solid. The basification procedure was carried out in triplicate. The average dried weight of solid product was 87.8 g±0.62 g. Using this average value, the weight of the crude solid sodium salts for the total organic acid solution was calculated to be 772.6 g, 95.3% yield by weight.

Example 19

Alcohol Precipitation of Combined Oxidation Products as Sodium Salts from Nitric Acid Oxidation Example 12, and Work up Procedure Example 15

A portion of dried solid crude sodium salt mixture (ca. 5.0 g) from Example 18, was dissolved in water (5 mL) to form a viscous amber solution. Methanol (50 mL) was added to the solution and a fine white precipitate form immediately. The mixture was stirred overnight during which time most of the syrup had solidified. The solid was isolated by filtration, washed with methanol (3×10 mL), and dried under reduced pressure. The filtrate and washings were combined, concentrated using a rotary evaporator, and dried under reduced pressure. The precipitation procedure was carried out in triplicate (18a-c, Table 6).

TABLE 6

| Sample | Initial Solid Weight (g) | Precipitate Weight (g) | Dried Filtrate Weight (g) | Recovered Solid Weight (g) |
|---|---|---|---|---|
| 18a | 5.0094 | 4.3130 | 0.8480 | 5.161 |
| 18b | 5.0078 | 4.0448 | 0.8704 | 4.9152 |
| 18c | 5.0073 | 4.3224 | 0.8650 | 5.1874 |

Example 20

Isolation of Monopotassium D-Glucarate (MPG) from Diffusion Dialysis Organic Acid Solution Organic acid stock solution (Example 16, 900 mL, 963.2 g) was concentrated using a rotary evaporator. The resulting yellow solution (175 mL, 208.2 g) was diluted to 300 mL. A portion of the solution (100 mL) was chilled in an ice bath and titrated from a pH of 1.8 to a pH of 3.7 with aqueous KOH (45% by weight). The solution was refrigerated overnight during which time a precipitate formed. The precipitate was isolated by filtration, washed with cold water (3×10 mL), and dried under reduced pressure to give MPG as a white powder. The precipitation procedure was carried out in triplicate. The average dried weight of solid product was 6.61 g±0.41 g. Using this average value, the weight of MPG for the total organic acid solution was calculated to be 72.7 g, 0.293 mol, 9.0% yield by weight.

Example 21

Isolation of Combined Oxidation Products, Less MPG in Example 20, as Potassium/Sodium Salts The filtrate and washings from the isolation of monopotassium D-glucarate (Example 20) were combined and chilled in an ice bath, then titrated from a pH of 3.8 to a pH of 10 with aqueous NaOH (11 mL, 45% w/w). The solution, which became amber in color, was allowed to warm to room temperature. The pH of the solution dropped over time but was maintained above 9 with additional NaOH (ca. 1 mL). The solution was refrigerated overnight resulting in a final pH of 9. The solution was concentrated using a rotary evaporator and dried under reduced pressure for 48 h to give a light brown, amorphous solid. The basification procedure was carried out in triplicate. The average dried weight of solid product was 59.4 g±0.82 g. Using this average value, the weight of the crude solid potassium/sodium salts for the total organic acid solution was calculated to be 653.4 g, 80.6% yield by weight.

Example 22

Isolation of Monopotassium Glucarate (MPG) from Diffusion Dialysis Reclaimed Acid A portion of the reclaimed nitric acid stock solution (40 mL, Example 16) was chilled in an ice bath and made basic with aqueous KOH (35 mL, 45% by weight). The solution was allowed to warm to room temperature and the pH was maintained above 9.5 with additional KOH. After stirring at room temperature for 5 h, the solution was cooled overnight. Crystals grew from the solution during this time. The crystals were isolated by filtration, washed with cold water (3×3 mL), and dried under reduced pressure to give potassium nitrate as colorless needles (5.80 g). The filtrate was chilled in an ice bath and back titrated to pH 3.7 with concentrated $HNO_3$ (8 mL). Precipitate formed when the pH of the solution fell below 5. The mixture was cooled overnight then the precipitate was isolated by filtration, washed with cold water (3×5 mL), and dried under reduced pressure to give MPG as a white powder (19.13 g). The weight of MPG for the total reclaimed nitric acid solution was calculated to be 100.21 g, 0.3670 mol, 12.4% yield by weight.

Example 23

Preparation of Sodium Potassium D-Glucarate from Monopotassium D-Glucarate, Procedure 1. (Styron, 2002)

Aqueous sodium hydroxide solution (33 mL, 6 M) was added to a slurry of monopotassium D-glucarate (50.0 g. 0.201 mol) in water (150 mL) until all of the solid dissolved and a constant pH of 9.7 was reached. The solution was concentrated to a syrup and seeded with the title compound. A solid crystalline cake formed over 24 h. The crystals were isolated by filtration, washed with cold 1:1 ethanol/water (3×15 mL), and dried under reduced pressure to give sodium potassium D-glucarate as colorless crystals (48.2 g, 0.157 mol as the dihydrate, 78.3%).

Example 24

Preparation of Sodium Potassium D-Glucarate from Monopotassium D-Glucarate Procedure 2. (Styron, 2002)

Aqueous sodium hydroxide solution (21 mL, 2 M) was added to a slurry of monopotassium D-glucarate (10.0 g, 40.3 mmol) in water (50 mL) until all of the solid dissolved and a constant pH of 10 was reached. The volume of the solution was reduced to 20 mL by rotary evaporator. Methanol (15 mL) was added, producing a cloudy solution which cleared upon heating. The solution was allowed to sit undisturbed at 5° C. Crystals grew from the solution over a 48 h period. The crystals were isolated by filtration, washed with cold 1:1 methanol/water (3×5 mL), and dried under reduced pressure to give sodium potassium D-glucarate as colorless crystals (10.2 g, 33.2 mmol as the dihydrate, 82.4%).

Example 25

Preparation of Dipotassium D-Glucarate from Monopotassium D-glucarate. (Styron, 2002)

Aqueous potassium hydroxide solution (27 mL, 2 M) was added to a slurry of monopotassium D-glucarate (10.2 g, 41.1 mmol) in water (50 mL) until all of the solid dissolved and a constant pH of 10 was reached. The solution was concentrated to a syrup and seeded with the title compound. Crystals grew slowly from the syrup. After two weeks, the crystals were isolated by filtration, washed with cold 1:1 ethanol/water (3×5 mL), and dried under reduced pressure to give dipotassium D-glucarate as colorless crystals (8.14 g, 26.8 mmol as the monohydrate, 65.1%).

It is understood that the foregoing examples are merely illustrative of the present invention. Certain modifications of the articles and/or methods employed may be made and still achieve the objectives of the invention. Such modifications are contemplated as within the scope of the claimed invention.

REFERENCES

1. U.S. Patent, Neiland, Wm. L.; Maguire, John J.; George, Charles B.; Kahler, Harry L. U.S. Pat. No. 2,529,177, Nov. 7, 1950.
2. U.S. Patent, Neiland, Wm. L.; Maguire, John J.; George, Charles B.; Kahler, Harry L. U.S. Pat. No. 2,529,178, Nov. 7, 1950.
3. Marukame, K.; Kandea, S. Fushoku Bumon linkai Shiryo (Nippon Xairyo Gakkai), journal written in Japanese, 173, 1-8, 1993. Chem. Abstr. AN 1993:543767.
4. Erasmus, Albert, German Patent (1970), DE 1929968, date Dec. 23, 1970 Chem. Abstr. AN 1971:478856.
5. Hashimoto, Tadashi; Kunihiko, Suzuki; Daigo, Hiroshi. Jpn. Tokkyo Koho (1976), Japanese Patent, JP 51041578, date Nov. 10, 1976 Chem. Abstr. AN 1977:458383.
6. Crambes, M.; Grangette, H.; Pivette, P.; Halcour, P.; U.S. Pat. No. 4,120,655, Oct. 17, 1978, Filed Jul. 11, 1977.
7. Mor, E.; Bonino, G., Annali dell'Universita di Ferrara, Sezione 5; Chimica Pura ed Applicata, 1971, Volume date 1970; Journal written in French, Chem. Abstr AN 1971:414090.
8. Mor, E. D.; Wrubl, C. Lab Corros. Mar. Met, British Corrosion Journal, 11, 199-203, 1976, Chem. Abstr. AN 1977:129710.
9. Wrubl, C.; Mor, E. D.; Ist Corros. Mar Met, British Corrosion Journal, 18, 142-7, 1983; Chem. Abstr. AN 1984:11228.
10. Kuczynski, E.; Michaelewshi, R.; Zyrek, D.; Baldys, M. Patent written in Polish, PL 98149, date Aug. 31, 1978 Chem. Abstr. AN 1979:495221.
11. Korzh, E. N.; Sukhotin, A. M.; Zhurnal Prikladnoi Khimii, Journal written in Russian, 54, 2404-2407, 1981, Chem. Abstr. AN1982-147045.
12. Sukhotin, A. M.; Borshchevskii, A. M.; Korzh, E. N.; Perel'shtein, I. I.; Arefeva, L. N.; Kuslyaikin, G. A.; Paushin, E. B.; Zashchita Mettalov, 18, 268-70, 1982, Journal written in Russian, Chem. Abstr. AN 1982:476671.
13. Abdallah, M.; Journal of the Electrochemical Society of India, 48, 121-127, 1999. Chem. Abstr. An 199:374923.
14. Foroulis, Z. A.; U.S. Pat. No. 3,589,859, date Jun. 29, 1971 Chem. Abstr. AN 1971:480174.
15. Foroulis, Z. A.; U.S. Pat. No. 3,711,246, date Jan. 16, 1973 Chem. Abstr. AN 1973:101854.
16. Foroulis, Z. A.; U.S. Pat. No. 4,108,790, date Aug. 22, 1978 Chem. Abstr. AN 1979:59223.
17. Foroulis, Z. A.; Patent written in German, DE 2,016,686, date Nov. 12, 1970 Chem. Abstr. An 1971:33980.
18. Foroulis, Z. A.; Patent written in French, FR 2054945, date Jun. 11, 1971 Chem. Abstr. An 1972:37332.
19. Foroulis, Z. A.; Patent written in French, FR 2,115,300, date Aug. 11, 1972 Chem. Abstr. AN 1973:139183.
20. Hiroshige, M.; Kondo, T.; Patent written in Japanese, JP 47048091, date Dec. 4, 1972 Chem. Abstr. AN 1973:539043.
21. Birk, E.; Krossner, L.; Hayn, W.; Pietsch, M.; Patent written in German (German Democratic Republic), DD 117492, date Jan. 12, 1976 Chem. Abstr. AN 1976:511905.
22. Ota, Y:, Sugano, R.; Murayama, S.; Patent written in Japanese, JP 54043840, date Apr. 6, 1979 Chem. Abstr. AN 1979:462555.
23. Abd El Kader, J. M.; El Warraky, A. A.; Abd El Aziz, A. M.; British Corrosion Journal, 33, 152-157, 1998. Chem. Abstr. AN 1998-796697.
24. Mishra, S. K.; Hanlon, D. J.; Bae, N-S.; U.S. Pat. No. 5,891,225, date Apr. 6, 1999 Chem. Abstr. 1999:224166.
25. Koefed, R. S.; U.S. Pat. No. 5,531,931, date Jul. 2, 1996 Chem. Abstr. 1996:452690.
26. Sufrin, B. W.; U.S. Pat. No. 5,330,683, date Jul. 19, 1994 Chem. Abstr. AN 1994:562268.
27. Koefod, Robert Scott, U.S. Patent, application, US 2007/0278446, Publication date, Dec. 7, 2007.
28. Wang, H.; Peop. Rep. China Patent, CN 1970488 A 20070530, Patent written in Chinese, Chem. Abstr. AN 2007:591031.
29. Roddy, C. W.; Chatterji, J.; Brenneis, D. C.; King, B. J.; U.S. Patent Application, App. US 2005-271431 20051110, Chem. Abstr. AN 2007:371507.
30. Drochon, B.; Komocki, S.; Michaux, M.; Brit. UK Patent Application, GB 2003-20938 20030908, Chem. Abstr. AN 2005:209612.
31. Boggs, B.; Rhodes, D.; U. S. Patent Application, US 2002-228008 20020826, Chem. Abstr. AN 2004:1048758.
32. Santra, A. K.; Luke, K., U.S. Patent Application, Cont.-in-part of U.S. Ser. No. 738,199, U.S. Application 2004-822459 20040412, Chem. Abstr. AN 2004:802044.
33. K.; Sakamoto, Y.; Maruyama, K.; Matsui, K.; Japanese Patent, Masuda, JP 2004123465, A 20040422, Patent written in Japanese, Chem. Abstr. AN 2004:330106.
34. Araki, A.; Miyaguchi, K.; Takahashi, A.; Terasaki, S.; Kushihashi, 1.; Japanese Patent, JP 2003306369 A 20031028, Chem. Abstr. AN 2003:841118.
35. Cerulli, T.; Clemente, P.; Ferrari, G.; Pistolesi, C.; Eur. Patent Application, EP 1201617 A1 20020503, Chem. Abstr. AN 2002:330240.
36. Wu, H.; Yang, J.; Peop. Rep. China Patent, CN 1131651 A 19960925, Patent written in Chinese, Chem. Abstr. AN 1999:604031.
37. Sekiguchi, M.; Sanada, M.; Matsui, A.; Japanese Patent, JP 04214057 A 19920805, Patent written in Japanese, Chem. Abstr. AN 1993:108530.
38. Sakurada, T.; Kotake, K.; Wakamya, T.; Watanabe, K.; Japanese Patent, JP 63248782 A 19881017, Patent written in Japanese, Chem. Abstr. AN 1989:159516.
39. Nakano, S.; Tada, S.; German Patent, DE 3519884 A1 19860130, Patent written in German, Chem. Abstr. AN 1986:154666.
40. Denki Kagaku Kyogyo K. K., Japan, Japanese Patent, JP 60112676 A 19850619, Patent written in Japanese, Chem. Abstr. AN 1985:565223.
41. Denki II Kagaku Kogyo K. K., Japanese Patent, Japan, JP 60108352 A 19850613, Chem. Abstr. AN 1985:528097.
42. Ene, N.; Popescu, F.; Vasioiu, P.; Romanian Patent, RO 69880 A2 19810430, Patent written in Romanian, Chem. Abstr. AN 1982:23967.
43. Walaszek, Z.; Hanausek-Walaszek, M.; Webb, T. and Minton, J. P.; U.S. Pat. No. 4,845,123, Jul. 4, 1989.
44. Walaszek, Z.; Slaga, T. J.; Hanausek-Walaszek, M.; U.S. Pat. No. 5,561,160, Oct. 1, 1996.
45. Walaszek, Z.; Slaga, T. J.; Hanausek-Walaszek, M.; U.S. Pat. No. 5,364,644, Nov. 15, 1994.
46. Styron, S. D.; French, A. D.; Freidrich, J. D.; Lake, C. H.; Kiely, D. E.; J. Carbohydr. Chem, 21, 27-51, 2002: dipotassium D-glucarate hydrate, $C_6H_{10}O_8K_2.H_2O$, Chem. Abstr Registry number 460054-47-1: Monosodium monopotassium D-glucarate dihydrate, hydrate $C_6H_{10}O_8KNa.2H_2O$, Chem. Abstr Registry number 460054-48-2.
47. Kiely, D. E.; Hash, K, U.S. Patent Application, US2008/0033205 A1, Feb. 7, 2008.
48. Kamlet, J.; U.S. Pat. No. 2,314,831, Mar. 23, 1943.
49. Stephanie Bringer-Meyer, K.; Hermann Sahm, J.; U.S. Pat. No. 5,017,485, May 21, 1991.

50. Tanaka, K.; Kimura, K.; U.S. Pat. No. 3,652,396, March 1972.
51. Wisconsin Biorefiners Development Initiative and references therein; Biorefining Processes—Fermentation of 6-Carbon Sugars and Starchs, http://www.wisbiorefine.org/proc/fermentss.pdf.
52. National Association of Corrosion Engineers (NACE) Standard TM0169-95 as Modified by the Pacific Northwest States, Test Method B, Revision 4-06.
53. Collepardi, M. M. in "Concrete Admixture Handbook: Properties, Science and Technology", $2^{nd}$ Edition, Ramachandran, V. S. Editor, Noyes Publications, Park Ridge, N.J. 07656, 1995, pp. 286-409.

The invention claimed is:

1. A method of preparing a deicing composition, the method comprising:
    a) preparing an aqueous solution of at least one organic compound suitable for nitric acid oxidation;
    b) combining, over time, the aqueous solution of the at least one organic compound and an aqueous solution of nitric acid to oxidize the at least one organic compound to a mixture of organic acids;
    c) removing a portion of the nitric acid from the combined aqueous solution through an evaporation process; and
    d) making basic with at least one base the solution from which nitric acid has been removed to convert residual nitric acid to inorganic nitrate and to convert the mixture of organic acids to a mixture of organic acid salts;
    wherein a deicing agent is combined with the residual inorganic nitrate and the mixture of organic acid salts.

2. The method of claim 1, wherein the deicing agent is selected from the group consisting of: sodium chloride, magnesium chloride, sodium acetate, potassium acetate, calcium magnesium acetate, and calcium chloride.

3. The method of claim 1, wherein the organic compound has two or more alcohol hydroxyl groups.

4. The method of claim 3, wherein the organic compound is glucose, xylose, fructose, glycerol, sorbitol, mannitol, maltose, lactose, cellobiose, maltotriose, maltotetrose, maltotetralose, sucrose, trehalose, stachyose, starch, cellulose, arabinogalactans, xylans, mannans, fructans or hemicelluloses.

5. The method of claim 4, wherein the organic compound is glucose, xylose, fructose, sucrose, starch or glycerol.

6. The method of claim 1, wherein at least one organic acid comprises glucaric acid, and the method further comprises the steps of, after step c): adding a potassium base to the solution from which nitric acid has been removed to neutralize residual nitric acid and to convert a portion of the glucaric acid to glucaric acid monopotassium salt; and removing at least some of the glucaric acid monopotassium salt from the at least one organic acid.

7. A method of preparing a deicing composition, the method comprising:
    a) preparing an aqueous solution of at least one organic compound suitable for nitric acid oxidation;
    b) combining, over time, the aqueous solution of the at least one organic compound and an aqueous solution of nitric acid to oxidize the at least one organic compound to a mixture of organic acids;
    c) removing a portion of the nitric acid from the combined aqueous solution through an evaporation process;
    d) making basic with at least one base the solution from which nitric acid has been removed to convert residual nitric acid to inorganic nitrate and to convert the mixture of organic acids to a mixture of organic acid salts; and
    e) isolating from the mixture of organic acid salts an organic acid salt;
    wherein a deicing agent is combined with the isolated organic acid salt or wherein a deicing agent is added to the mixture of organic acid salts and residual inorganic nitrate after isolating from the mixture of organic acid salts an organic acid salt.

8. The method of claim 7, wherein the isolated organic acid salt is a glucaric acid salt.

9. The method of claim 7, wherein the deicing agent is selected from the group consisting of: sodium chloride, magnesium chloride, sodium acetate, potassium acetate, calcium magnesium acetate, and calcium chloride.

10. The method of claim 7, wherein the organic compound has two or more alcohol hydroxyl groups.

11. The method of claim 10, wherein the organic compound is glucose, xylose, fructose, glycerol, sorbitol, mannitol, maltose, lactose, cellobiose, maltotriose, maltotetrose, maltotetralose, sucrose, trehalose, stachyose, starch, cellulose, arabinogalactans, xylans, mannans, fructans or hemicelluloses.

12. The method of claim 11, wherein the organic compound is glucose, xylose, fructose, sucrose, starch or glycerol.

13. The method of claim 7, wherein at least one organic acid comprises glucaric acid, and the method further comprises the steps of, after step c): adding a potassium base to the solution from which nitric acid has been removed to neutralize residual nitric acid and to convert a portion of the glucaric acid to glucaric acid monopotassium salt; and removing at least some of the glucaric acid monopotassium salt from the at least one organic acid.

14. A method of preparing a deicing composition, the method comprising:
    a) preparing an aqueous solution of at least one organic compound suitable for nitric acid oxidation;
    b) combining, over time, the aqueous solution of the at least one organic compound and an aqueous solution of nitric acid to oxidize the at least one organic compound to a mixture of organic acids;
    c) removing a portion of the nitric acid from the combined aqueous solution through an evaporation process;
    d) making basic with at least one base the solution from which nitric acid has been removed to convert residual nitric acid to inorganic nitrate and to convert the mixture of organic acids to a mixture of organic acid salts; and
    e) isolating the mixture of organic acid salts as an amorphous solid;
    wherein a deicing agent is combined with the amorphous solid.

15. The method of claim 14, wherein the deicing agent is selected from the group consisting of: sodium chloride, magnesium chloride, sodium acetate, potassium acetate, calcium magnesium acetate, and calcium chloride.

16. The method of claim 14, wherein the organic compound has two or more alcohol hydroxyl groups.

17. The method of claim 16, wherein the organic compound is glucose, xylose, fructose, glycerol, sorbitol, mannitol, maltose, lactose, cellobiose, maltotriose, maltotetrose, maltotetralose, sucrose, trehalose, stachyose, starch, cellulose, arabinogalactans, xylans, mannans, fructans or hemicelluloses.

18. The method of claim 17, wherein the organic compound is glucose, xylose, fructose, sucrose, starch or glycerol.

19. The method of claim 14, wherein at least one organic acid comprises glucaric acid, and the method further comprises the steps of, after step c): adding a potassium base to the solution from which nitric acid has been removed to neutralize residual nitric acid and to convert a portion of the glucaric acid to glucaric acid monopotassium salt; and removing at least some of the glucaric acid monopotassium salt from the at least one organic acid.

20. A method of preparing a deicing composition, the method comprising:
   a) preparing an aqueous solution of at least one organic compound suitable for nitric acid oxidation;
   b) combining, over time, the aqueous solution of the at least one organic compound and an aqueous solution of nitric acid to oxidize the at least one organic compound to a mixture of organic acids;
   c) removing a portion of the nitric acid from the combined aqueous solution through an evaporation process;
   d) making basic with at least one base the solution from which nitric acid has been removed to convert residual nitric acid to inorganic nitrate and to convert the mixture of organic acids to a mixture of organic acid salts;
   e) isolating the mixture of organic acid salts as an amorphous solid;
   f) dissolving at least a portion of the amorphous solid in a solvent;
   g) precipitating a solid precipitate from the solvent, the solid precipitate comprising one or more hydroxycarboxylic acid salts; and
   h) recovering the solid precipitate;
   wherein a deicing agent is combined with the recovered solid precipitate.

21. The method of claim 20, wherein the deicing agent is selected from the group consisting of: sodium chloride, magnesium chloride, sodium acetate, potassium acetate, calcium magnesium acetate, and calcium chloride.

22. The method of claim 20, wherein the organic compound has two or more alcohol hydroxyl groups.

23. The method of claim 22, wherein the organic compound is glucose, xylose, fructose, glycerol, sorbitol, mannitol, maltose, lactose, cellobiose, maltotriose, maltotetrose, maltotetralose, sucrose, trehalose, stachyose, starch, cellulose, arabinogalactans, xylans, mannans, fructans or hemicelluloses.

24. The method of claim 23, wherein the organic compound is glucose, xylose, fructose, sucrose, starch or glycerol.

25. The method of claim 20, wherein at least one organic acid comprises glucaric acid, and the method further comprises the steps of, after step c): adding a potassium base to the solution from which nitric acid has been removed to neutralize residual nitric acid and to convert a portion of the glucaric acid to glucaric acid monopotassium salt; and removing at least some of the glucaric acid monopotassium salt from the at least one organic acid.

* * * * *